US012760274B2

(12) United States Patent
Zhao et al.

(10) Patent No.: US 12,760,274 B2
(45) Date of Patent: Oct. 13, 2026

(54) COMPOSITIONS AND METHODS OF STIMULATING AND EXPANDING T CELLS

(71) Applicant: The Trustees of the University of Pennsylvania, Philadelphia, PA (US)

(72) Inventors: Yangbing Zhao, Lumberton, NJ (US); Xiaojun Liu, Wallingford, PA (US); Carl H. June, Merion Station, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1004 days.

(21) Appl. No.: 17/932,188

(22) Filed: Sep. 14, 2022

(65) Prior Publication Data

US 2023/0110342 A1 Apr. 13, 2023

Related U.S. Application Data

(62) Division of application No. 15/521,741, filed as application No. PCT/US2015/058228 on Oct. 30, 2015, now Pat. No. 11,471,487.

(60) Provisional application No. 62/073,268, filed on Oct. 31, 2014.

(51) Int. Cl.

| | |
|---|---|
| ***C12N 5/0783*** | (2010.01) |
| ***A01N 1/10*** | (2025.01) |
| ***A61K 40/11*** | (2025.01) |
| ***A61K 40/31*** | (2025.01) |
| ***A61K 40/32*** | (2025.01) |
| ***A61K 40/42*** | (2025.01) |
| ***A61K 48/00*** | (2006.01) |
| ***C07K 14/705*** | (2006.01) |
| ***C07K 14/715*** | (2006.01) |
| ***C07K 14/725*** | (2006.01) |
| ***C07K 16/28*** | (2006.01) |
| ***C07K 16/30*** | (2006.01) |
| *A61K 35/12* | (2015.01) |
| *A61K 39/00* | (2006.01) |

(52) U.S. Cl.

CPC ............ *C12N 5/0636* (2013.01); *A01N 1/10* (2025.01); *A61K 40/11* (2025.01); *A61K 40/31* (2025.01); *A61K 40/32* (2025.01); *A61K 40/4205* (2025.01); *A61K 40/4211* (2025.01); *A61K 40/4269* (2025.01); *A61K 48/00* (2013.01); *C07K 14/705* (2013.01); *C07K 14/7051* (2013.01); *C07K 14/70517* (2013.01); *C07K 14/70521* (2013.01); *C07K 14/70596* (2013.01); *C07K 14/7151* (2013.01); *C07K 16/2809* (2013.01); *C07K 16/30* (2013.01); *A61K 2035/124* (2013.01); *A61K 2039/505* (2013.01); *A61K 2239/31* (2023.05); *A61K 2239/38* (2023.05); *C07K 2317/622* (2013.01); *C07K 2319/02* (2013.01); *C07K 2319/03* (2013.01); *C12N 2501/51* (2013.01); *C12N 2510/00* (2013.01)

(58) Field of Classification Search

CPC ...................................................... A61K 40/31

See application file for complete search history.

(56) References Cited

U.S. PATENT DOCUMENTS

| | | | |
|---|---|---|---|
| 4,444,887 | A | 4/1984 | Hoffmann |
| 4,716,111 | A | 12/1987 | Osband et al. |
| 4,816,567 | A | 3/1989 | Cabilly |
| 5,199,942 | A | 4/1993 | Gillis |
| 5,225,539 | A | 7/1993 | Winter |
| 5,229,275 | A | 7/1993 | Goroff |
| 5,350,674 | A | 9/1994 | Boenisch |
| 5,413,923 | A | 5/1995 | Kucherlapati |
| 5,530,101 | A | 6/1996 | Queen |
| 5,545,806 | A | 8/1996 | Lonberg |
| 5,565,332 | A | 10/1996 | Hoogenboom |
| 5,567,610 | A | 10/1996 | Borrebaeck |
| 5,569,825 | A | 10/1996 | Lonberg |
| 5,573,905 | A | 11/1996 | Lerner |
| 5,585,089 | A | 12/1996 | Queen |
| 5,585,362 | A | 12/1996 | Wilson |
| 5,625,126 | A | 4/1997 | Lonberg |
| 5,626,561 | A | 5/1997 | Butler |
| 5,633,425 | A | 5/1997 | Lonberg |
| 5,661,016 | A | 8/1997 | Lonberg |
| 5,787,900 | A | 8/1998 | Butler |

(Continued)

FOREIGN PATENT DOCUMENTS

| | | |
|---|---|---|
| CN | 102112495 | 6/2011 |
| CN | 102770451 | 11/2012 |

(Continued)

OTHER PUBLICATIONS

Zhao, Y., et al., "Multiple Injections of Electroporated Autologous T Cells Expressing a Chimeric Antigen Receptor Mediate Regression of Human Disseminated Tumor", Cancer Res; 70(22); 9053-61, 2010.

(Continued)

*Primary Examiner* — Arthur S Leonard

(74) *Attorney, Agent, or Firm* — Saul Ewing LLP; Alireza Behrooz; Kathryn Doyle

(57) ABSTRACT

The present invention includes a method for expanding a population of electroporated T cells. The method includes electroporating a population of cells comprising T cells with mRNA encoding a chimeric membrane protein comprising an antigen binding domain to a molecule and an intracellular domain of a co-stimulatory molecule, wherein the cultured T cells expand at least 10 fold. The invention further includes an expanded population of T cells, compositions comprising the cells and methods of treatment.

11 Claims, 16 Drawing Sheets

Specification includes a Sequence Listing.

(56) References Cited

U.S. PATENT DOCUMENTS

| | | | |
|---|---|---|---|
| 5,814,318 | A | 9/1998 | Lonberg |
| 5,843,069 | A | 12/1998 | Butler |
| 5,902,745 | A | 5/1999 | Butler |
| 5,913,998 | A | 6/1999 | Butler |
| 5,939,598 | A | 8/1999 | Kucherlapati |
| 5,980,889 | A | 11/1999 | Butler |
| 5,993,434 | A | 11/1999 | Dev |
| 6,120,766 | A | 9/2000 | Hale |
| 6,181,964 | B1 | 1/2001 | Hofmann |
| 6,233,482 | B1 | 5/2001 | Hofmann |
| 6,241,701 | B1 | 6/2001 | Hofmann |
| 6,331,415 | B1 | 12/2001 | Cabilly |
| 6,516,223 | B2 | 2/2003 | Hofmann |
| 6,548,640 | B1 | 4/2003 | Winter |
| 6,567,694 | B2 | 5/2003 | Hayakawa |
| 6,678,556 | B1 | 1/2004 | Nolan |
| 7,171,264 | B1 | 1/2007 | Hofmann |
| 7,173,116 | B2 | 2/2007 | Fewell |
| 2004/0014645 | A1 | 1/2004 | Draghia-Akli |
| 2004/0059285 | A1 | 3/2004 | Mathiesen |
| 2004/0092907 | A1 | 5/2004 | Mathiesen |
| 2005/0052630 | A1 | 3/2005 | Smith |
| 2005/0070841 | A1 | 3/2005 | Mathiesen |
| 2006/0034810 | A1 | 2/2006 | Riley |
| 2007/0128708 | A1 | 6/2007 | Gamelin |
| 2013/0164272 | A1 | 6/2013 | Kammula |
| 2014/0099309 | A1 | 4/2014 | Powell, Jr. |
| 2015/0299656 | A1 | 10/2015 | Gattinoni |

FOREIGN PATENT DOCUMENTS

| | | | |
|---|---|---|---|
| EP | 239400 | A2 | 9/1987 |
| EP | 519596 | A1 | 12/1992 |
| EP | 592106 | A1 | 4/1994 |
| WO | 9109967 | A1 | 7/1991 |
| WO | 9110741 | A1 | 7/1991 |
| WO | 9633735 | A1 | 10/1996 |
| WO | 9634096 | A1 | 10/1996 |
| WO | 9816654 | A1 | 4/1998 |
| WO | 9824893 | A2 | 6/1998 |
| WO | 9846645 | A2 | 10/1998 |
| WO | 9850433 | A2 | 11/1998 |
| WO | 2012079000 | A1 | 6/2012 |
| WO | 2013123061 | A1 | 8/2013 |
| WO | 2013169691 | | 11/2013 |

OTHER PUBLICATIONS

Willinger et al., Molecular signatures distinguish human central memory from effector memory CD8 T cell subsets (J Immuno, 2005, 175:5895-5903) (Year: 2005).

Wu, et al., "Humanization of a murine monoclonal antibody by simultaneous optimization of framework and CDR residues", J. Mol. Biol., 294:151-162 (1999).

Xiao-Song Zhong et al., "Chimeric Antigen Receptors Combining 4-1BB and CD28 Signaling Domains Augment PI3kinase/AKT/Bcl-XL Activation and CD8+ T Cell-mediated Tumor Eradication", Molecular Therapy, (Feb. 1, 2010), vol. 18, No. 2, doi: 10.1038/mt.2009.210, ISSN 1525-0016, pp. 413-420, XP055023623.

Zhao, et al., "Multiple injections of electroporated autologous T cells expressing a chimeric antigen receptor mediate regression of human disseminated tumor", Cancer Res. Nov. 15, 2010; 70(22): 9053-9061.

Ang et al., Avoiding the Need for Clinical-Grade OKT3: Ex Vivo Expansion of T Cells Using Artificial Antigen Presenting Cells Genetically Modified to Cross-Link CD3. Biology of Blood and Marrow Transplantation. vol. 18, Issue 2, Supplement, S258, Feb. 1, 2012 (Year: 2012).

Bierer et al., "Cyclosporin A and FK506: molecular mechanisms of immunosuppression and probes for transplantation biology." Curr. Opin. Immun. 5:763-773, 1993.

Bird, et al., "Single-chain antigen-binding proteins", 1988, Science 242:423-426.

Bruggermann , et al., "Designer Mice: The Production of Human Antibody Repertoires in Transgenic Animals.", Year in Immunol., 7:33-40 (1993).

Carter, et al., "Humanization of an anti-p185HER2 antibody for human cancer therapy", Proc. Natl. Acad. Sci. 89, 1992, 4285-4289.

Chatenoud et al., Anti-CD3 antibody induces long-term remission of overt autoimmunity in nonobese diabetic mice. Proc. Natl. Acad. Sci. USA vol. 91, pp. 123-127, Jan. 1994 (Year: 1994).

Chothia, et al., "Canonical structures for the hypervariable regions of immunoglobulins", J Mol Biol. Aug. 20, 1987; 196(4):901-17. (Abstract).

Clackson, et al., "Making antibody fragments using phage display libraries", 1991, Nature 352:624-628.

Cougot, et al., "Cap-tabolism", Trends in Biochem. Sci., 29:436-444 (2001) (abstract).

Duchosal, et al., "Immunization of hu-PBL-SCID mice and the rescue of human monoclonal Fab fragments through Combinatorial libraries", 1992, Nature 355:258-262.

Dudley, et al., "Generation of tumor-infiltrating lymphocyte cultures for use in adoptive transfer therapy for melanoma patients", J Immunother. Jul.-Aug. 2003;26(4), Jul.-Aug. 2003, 332-342.

Elango, et al., "Optimized transfection of mRNA transcribed from a d(A/T) 100 tail-containing vector", Biochim. Biophys. Res. Commun., 330:958-966 (2005) (abstract).

European Patent Application No. 15855976.5—European Search Report dated May 11, 2018.

Griffiths , et al., "Human anti-self antibodies with high specificity from phage display libraries.", The EMBO Journal vol. 12, No. 2, pp. 725-734, 1993.

Henderson , et al., "Comparison of the effects of FK-506, cyclosporin A and rapamycin on IL-2 production.", Immun 73:316-321, 1991.

Hoogenboom et al., "By-passing immunization. Human antibodies from synthetic repertoires of germline VH gene segments rearranged in vitro." J. Mol. Biol., 227:381-8 (1991) (abstract).

Huls et al., Clinical Application of Sleeping Beauty and Artificial Antigen Presenting Cells to Genetically Modify T Cells from Peripheral and Umbilical Cord Blood. J. Vis. Exp. (72), e50070, doi: 10.3791/50070 (2013) (Year: 2013).

Huston et al., "Protein engineering of antibody binding sites: Recovery of specific activity in an anti-digoxin single-chain Fv analogue produced in *Escherichia coli*.", 1988, Proc Natl Acad Sci USA 85:5879-5883.

International Search Report and Written Opinion dated Feb. 4, 2016—PCT/US2015/058228.

Jakobovits, et al., "Analysis of homozygous mutant chimeric mice: Deletion of the immunoglobulin heavy-chain joining region blocks B-cell development and antibody production", Proc. Natl. Acad. Sci. 90, 1993, 2551-2555.

Jakobovits, et al., "Germ-line transmission and expression of a human-derived yeast artificial chromosome", Nature, 362:255-258 (1993).

Johnson, et al., "Human antibody engineering", Current Opinion in Structural Biology 3:564-571 (1993).

Jones, et al., "Replacing the complementarity-determining regions in a human antibody with those from a mouse", Nature, 321:522-525 (1986).

Liu Xiaojun et al., "Novel T cells with improvedin vivoanti-tumor activity generated by RNA electroporation", Protein & Cell, Springer Asia, Beijing, CN, vol. 8, No. 7, doi: 10.1007/S13238-017-0422-6, ISSN 1674-800X, (May 18, 2017), pp. 514-526, (May 18, 2017), XP036271573.

Liu, et al., "Calcineurin is a common target of cyclophilin-cyclosporin A and FKBP-FK506 complexes", Cell 66:807-815, 1991.

Marks , et al., "By-passing immunization. Human antibodies from V-gene libraries displayed on phage", J. Mol. Biol. 222:581-597 (1991).

Mccafferty, et al., "Phage antibodies: filamentous phage displaying antibody variable domains", Nature 348, 1990, 552-554.

(56) References Cited

OTHER PUBLICATIONS

Nacheva, et al., “Preventing nondesired RNA-primed RNA extension catalyzed by T7 RNA polymerase”, Eur. J. Biochem., 270:1485-65 (2003).
Nakagawa, et al., “Development of next-generation adoptive immunotherapy using cytotoxic T-lymphocyte (CTL) expressing chimeric antigen-rectpor (CAR)”, Drug Delivery System, 2013, vol. 28, pp. 35-44 (partial translation provided).
Nishikawa, et al., “Nonviral vectors in the new millennium: delivery barriers in gene transfer”, Hum. Gene Ther., 12(8):861-70 (2001) (abstract).
Padlan, “A possible procedure for reducing the immunogenicity of antibody variable domains while preserving their ligand-binding properties.” 1991, Molecular Immunology, 28(4/5):489-498.
Panka et al., Variable region framework differences result in decreased or increased affinity of variant anti-digoxin antibodies. PNAS, 1988, 85:3080-3084. (Year: 1988).
Presta, et al., “Humanization of an antibody directed against IgE”, J. Immunol., 151:2623-32(1993).
Presta, et al., Antibody engineering., Current Opinion in Biotechnology 1992, 3:394-398.
Riechmann , “Single domain antibodies: comparison of camel VH and camelised human VH domains”, 1999, Journal of Immunological Methods 231:25-38.
Riechmann, et al., “Reshaping human antibodies for therapy”, Nature, 332:323-327 (1988).
Riley, J. L., “PD-1 signaling in primary T cells”, Immunol. Rev., (2009), vol. 229, doi: 10.1111/j.1600-065X.2009.00767.x, ISSN 0004347118, pp. 114-125, XP055402866.
Roder, et al., “The EBV-hybridoma technique”, Methods Enzymol., 121:140-167 (1986).
Roguska, et al., Humanization of murine monoclonal antibodies through variable domain resurfacing, PNAS, 91:969-973 (1994).
Rosenberg et al., “Use of tumor-infiltrating lymphocytes and interleukin-2 in the immunotherapy of patients with metastatic melanoma. A preliminary report.” New Eng. J. of Med. 319:1676-80, 1988.
Rudikoff, S., et al., “Single amino acid substitution altering antigen-binding specificity”, Proc Natl Acad Sci USA, vol. 79, pp. 1979-1983, 1982.
Schenborn, et al., “A novel transcription property of SP6 and T7 RNA polymerases: dependence on template structure”, Nuc. Acids Res., 13:6223-36 (1985).
Sims, et al., “A humanized CD18 antibody can block function without cell destruction”, J. Immunol., 151:2296-2308 (1993).
Skerra, et al., “Assembly of a Functional Immunoglobulin Fv Fragment in Escherichia coli”, Science, 240, 1988, 1038-1041.
Stepinski, et al., “Synthesis and properties of mRNAs containing the novel “anti-reverse” cap analogs 7-methyl(3'-0-methyl)GpppG and 7-methyl(3'-deoxy)GpppG”, RNA, 7:1468-95 (2001).
Studnicka, et al., “Human-engineered monoclonal antibodies retain full specific binding activity by preserving non-CDR complementarity-modulating residues”, Protein Engineering, 7(6):805-814 (1994).
Tsoukas et al., Activation of resting T lymphocytes by anti-CD3 (T3) antibodies in the absence of monocytes. J Immunol; Sep. 1, 1985, 135(3);1719-1723 (Year: 1985).
Vaughan, et al., “Human antibodies with sub-nanomolar affinities isolated from a large non-immunized phage display library”, Nature Biotech., 14:309-14 (1996) (abstract).
Verhoeyen, et al., “Reshaping human antibodies: grafting an antilysozyme activity”, Science, 239:1534-1536 (1988).
Ward, et al., “Binding activities of a repertoire of single immunoglobulin variable domains secreted from *Escherichia coli*.” Nature 341:544-546 (1989).

| | OKT-28bb | CD86 | CD83 | 4-1BBL | PD1-CD28 | IL-21 |
|---|---|---|---|---|---|---|
| OKT-28bb-1 | √ | | | | | |
| OKT-28bb-2 | √ | √ | | √ | | |
| OKT-28bb-3 | √ | √ | | √ | √ | √ |
| OKT-28bb-4 | √ | √ | | √ | √ | |
| OKT-28bb-5 | √ | √ | √ | | √ | |
| OKT-28bb-6 | √ | √ | √ | | √ | √ |

Figure 10

COMPOSITIONS AND METHODS OF STIMULATING AND EXPANDING T CELLS

CROSS-REFERENCE TO RELATED APPLICATIONS

The present application is a divisional of Ser. No. 15/521,741, filed Apr. 25, 2017, which is a 35 U.S.C. § 371 national phase application from, and claims priority to, International Application No. PCT/US2015/058228, filed Oct. 30, 2015, which claims priority under 35 U.S.C. § 119(e) to U.S. Provisional Application No. 62/073,268, filed Oct. 31, 2014, all of which applications are incorporated herein by reference in their entireties.

REFERENCE TO SEQUENCE LISTING

The Sequence Listing submitted herewith as a xml file named "046483-7035US2(03007)) Sequence Listing," created on Sep. 7, 2022 and having a size of 14,127 bytes, is incorporated herein by reference in its entirety.

STATEMENT REGARDING FEDERALLY SPONSORED RESEARCH OR DEVELOPMENT

This invention was made with government support under CA120409 awarded by the National Institute of Health. The government has certain rights in the invention.

BACKGROUND OF THE INVENTION

Adoptive cell transfer of genetically engineered T cells has been proven to be an attractive alternative for cancer treatment. However, T cells must generally be expanded before sufficient numbers can be manipulated for treatment. There are multiple ways that can be used in the clinical setting to stimulate and expand T cells, including stimulation with anti-CD3/CD28 beads, stimulation with anti-CD3 with or without anti-CD28 antibody, and cell based artificial stimulation with antigen presenting cells. T cells generated by these different methods display different phenotypes and in vitro/in vivo functions.

Therefore a need exists in the art for improved methods to derive populations of T cells for the purpose of generating T cells that could maximally exert their effector functions in vivo for T cell based adoptive immunotherapy.

SUMMARY OF THE INVENTION

As described herein, the present invention relates to compositions and methods for stimulating and expanding T cells.

One aspect of the invention includes a method for expanding a population of T cells, the method comprising electroporating a population of cells comprising T cells with mRNA encoding a chimeric membrane protein, the chimeric membrane protein comprising an extracellular domain comprising an antigen binding domain comprising an antibody or fragment thereof to a molecule and an intracellular domain comprising a fragment of an intracellular domain of CD28 and 4-1BB, wherein the mRNA is introduced into at least one of the cells in the population and expressed on the surface of the cells, and culturing the electroporated population of cells, wherein the T cells contained therein expand at least 10 fold.

In another aspect, the invention includes a method for expanding a population of electroporated T cells, the method comprising electroporating a population of cells comprising T cells with mRNA encoding a chimeric membrane protein, the chimeric membrane protein comprising a single chain variable fragment (scFv) directed against CD3 and an intracellular domain comprising a fragment of an intracellular domain of CD28 and 4-1BB, wherein the mRNA is introduced into at least one of the cells in the population and expressed on the surface of the cells, and culturing the electroporated population of cells, wherein the T cells contained therein expand at least 10 fold.

In yet another aspect, the invention includes a T cell comprising an electroporated mRNA encoding a chimeric membrane protein comprising a single chain variable fragment (scFv) directed against CD3 and an intracellular domain comprising a fragment of an intracellular domain of CD28 and 4-1BB.

In another aspect, the invention includes a population of electroporated T cells comprising an electroporated mRNA encoding a chimeric membrane protein comprising an extracellular domain comprising an antigen binding domain comprising an antibody or fragment thereof to a molecule, and an intracellular domain comprising a fragment of an intracellular domain of CD28 and 4-1BB.

Another aspect of the invention includes a method for adoptive cell transfer therapy comprising administering an expanded population of cells comprising T cells to a subject in need thereof to prevent or treat an immune reaction that is adverse to the subject, wherein the expanded population of cells has been expanded according to a method comprising electroporating a population of cells comprising T cells with mRNA encoding a chimeric membrane protein comprising single chain variable fragment (scFv) directed against CD3 and an intracellular domain comprising a fragment of an intracellular domain of CD28 and 4-1BB, wherein at least one of the cells in the population expresses the chimeric membrane protein; and culturing the cell population, wherein the T cells contained therein expand at least 10 fold.

Still another aspect of the invention includes a method of treating a disease or condition associated with enhanced immunity in a subject comprising administering an expanded population of cells comprising T cells to a subject in need thereof, wherein the expanded population of cells has been expanded according to a method comprising electroporating a population of cells comprising T cells with mRNA encoding a chimeric membrane protein comprising single chain variable fragment (scFv) directed against CD3 and an intracellular domain comprising a fragment of an intracellular domain of CD28 and 4-1BB, wherein at least one of the cells in the population expresses the chimeric membrane protein; and culturing the population, wherein the T cells contained therein expand at least 10 fold.

In another aspect, the invention includes an expanded T cell population made by the methods described herein.

In yet another aspect, a method of treating a condition in a subject, comprising administering to the subject a therapeutically effective amount of a pharmaceutical composition comprising the modified T cell generated in the method described herein.

In still another aspect, the invention includes a use of the T cell described herein in the manufacture of a medicament for the treatment of an immune response in a subject in need thereof.

In various embodiments of the above aspects or any other aspect of the invention delineated herein, the population of cells to be electroporated is selected from the group consisting of peripheral blood mononuclear cells, cord blood cells, a purified population of T cells, and a T cell line. In another embodiment, the population of cells to be electroporated comprises peripheral blood mononuclear cells. In yet another embodiment, the population of cells to be electroporated comprises purified T cells.

In one embodiment, the mRNA comprises in vitro transcribed RNA or synthetic RNA. In another embodiment, the mRNA encoding the chimeric membrane protein further comprises transmembrane domain. In yet another embodiment, the mRNA encoding the chimeric membrane protein further comprises a hinge domain.

In another embodiment, the antibody is selected from the group consisting of a synthetic antibody, human antibody, humanized antibody, single domain antibody, single chain variable fragment, and antigen-binding fragments thereof. In yet another embodiment, the antigen binding domain is selected from the group consisting anti-CD3, anti-TCR, anti-CD28, and a combination thereof.

In yet another embodiment, at least one cell in the population of cells expresses CD3. Tn another embodiment, at least one cell expressing the chimeric membrane protein interacts with another cell expressing CD3.

In yet another embodiment, the T cells expand in the range of about 20 fold to about 50 fold.

In one embodiment, the method described herein further comprises electroporating a mRNA encoding an agent into the expanded population of T cells. In another embodiment, the agent mRNA is co-electroporated with the chimeric membrane protein mRNA. In yet another embodiment, the method described herein further comprises stimulating the expanded population of T cells with at least one molecule or cytokine selected from the group consisting of CD27, CD28, CD83, CD86, CD127, 4-1BBL IL2, IL21, IL-15, IL-7, PD1-CD28 and PD1. In another embodiment, the method described herein further comprises cryopreserving the cultured T cells.

In another embodiment, the immune response is an autoimmune disease. In yet another embodiment the autoimmune disease is selected from the group consisting of Acquired Immunodeficiency Syndrome (AIDS), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/giant cell arteritis, ulcerative colitis, uveitis, vitiligo, Wegener's granulomatosis, and any combination thereof.

In another embodiment, the immune response is a cancer. In yet another embodiment, the cancer is selected from the group consisting of breast cancer, prostate cancer, ovarian cancer, cervical cancer, skin cancer, pancreatic cancer, colorectal cancer, renal cancer, liver cancer, brain cancer, lymphoma, leukemia, lung cancer, and thyroid carcinoma.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 10 is a table detailing the RNA co-electroporations. OKT-28BB-1: T cells expanded by electroporation of PBMCs with only OKT-28BB RNA. OKT-28BB-2 to OKT-28BB-6: T cells expanded by co-electroporation of PBMCs with OKT-28BB and different combinations of RNA encoding other molecules shown.

DETAILED DESCRIPTION

Definitions

Figure 1:
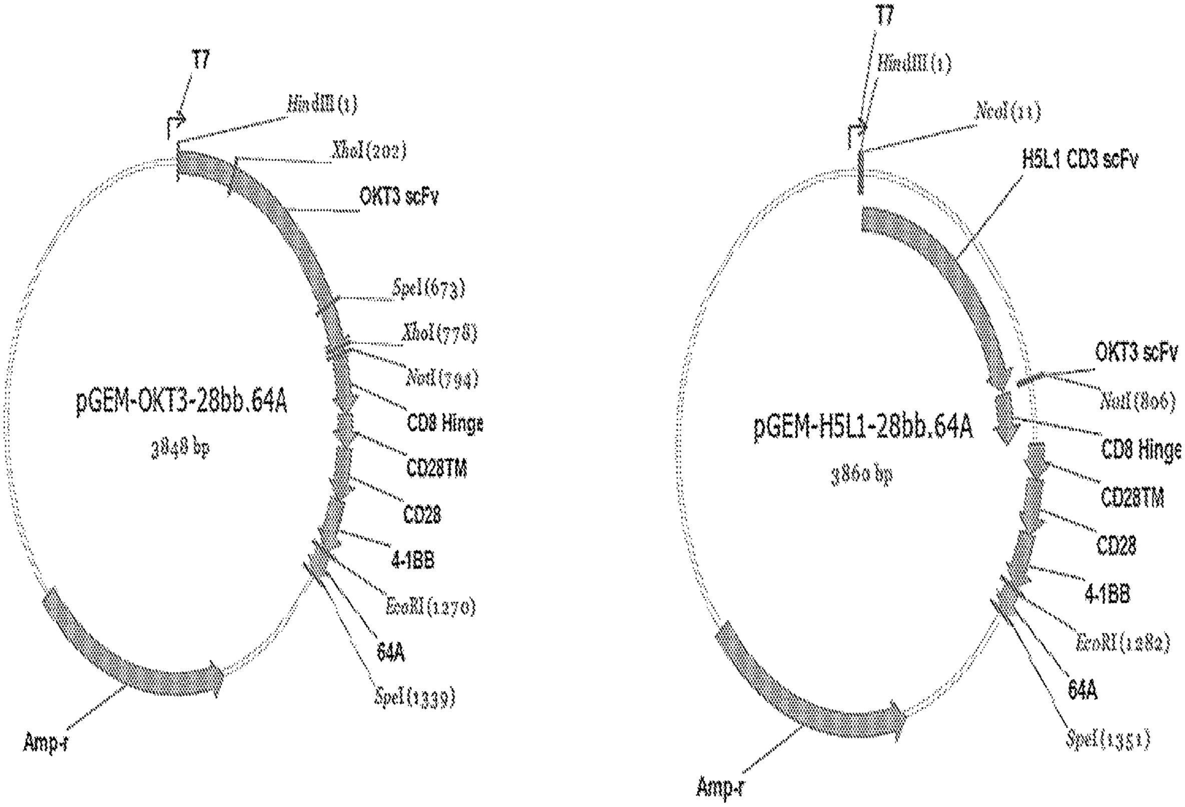
FIG. 1 is a panel of vector maps of anti-CD3-H5L1-28BB and anti-CD3-OKT3-28BB. In both constructs, anti-CD3 scFv were fused with CD8 hinge region followed by CD28 transmembrane, CD28 intracellular and 4-1BB intracellular regions.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of +20% or ±10%, more preferably ±5%, even more preferably ±1%, and still more preferably ±0.1% from the specified value, as such variations are appropriate to perform the disclosed methods.

The term "antibody," as used herein, refers to an immunoglobulin molecule which specifically binds with an antigen. Antibodies can be intact immunoglobulins obtained from natural sources or from recombinant sources and can be immunoreactive portions of intact immunoglobulins. Antibodies are typically tetramers of immunoglobulin molecules. Tetramers may be naturally occurring or reconstructed from single chain antibodies or antibody fragments. Antibodies also include dimers that may be naturally occurring or constructed from single chain antibodies or antibody fragments. The antibodies in the present invention may exist in a variety of forms including, for example, polyclonal antibodies, monoclonal antibodies, Fv, Fab and $F(ab')_2$, as well as single chain antibodies (scFv), humanized antibodies, and human antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to a region of an intact antibody and refers to the antigenic determining variable regions of an intact antibody. Examples of antibody fragments include, but are not limited to, Fab, Fab', $F(ab')_2$, and Fv fragments, linear antibodies, scFv antibodies, single-domain antibodies, such as camelid antibodies (Riechmann, 1999, Journal of Immunological Methods 231:25-38), composed of either a VL or a VH domain which exhibit sufficient affinity for the target, and multispecific antibodies formed from antibody fragments. The antibody fragment also includes a human antibody or a humanized antibody or a fragment of a human antibody or a humanized antibody thereof.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. $\alpha$ and $\beta$ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be generated from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated, synthesized or originate from a biological sample. Such a biological sample can include, but is not limited to a tissue sample, a tumor sample, a cell or a biological fluid.

As used herein, the term "autologous" is meant to refer to any material originating from the same individual to which it is later to be re-introduced into the individual.

"Allogeneic" refers to a graft derived from a different animal of the same species.

"Xenogencic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer, thyroid cancer, and the like.

The term "chimeric antigen receptor" or "CAR," as used herein, refers to an artificial T cell receptor that is engineered to be expressed on an immune effector cell and specifically bind an antigen. CARs may be used as a therapy with adoptive cell transfer. T cells are removed from a patient and modified so that they express the receptors specific to a particular form of antigen. In some embodiments, the CARs have been expressed with specificity to a tumor associated antigen, for example. CARs may also comprise an intracellular activation domain, a transmembrane domain and an extracellular domain comprising a tumor associated antigen binding region. In sonic aspects, CARs comprise fusions of single-chain variable fragments (scFv) derived monoclonal antibodies, fused to CD3-zeta transmembrane and intracellular domain. The specificity of CAR designs may be derived from ligands of receptors (e.g., peptides). In some embodiments, a CAR can target cancers by redirecting the specificity of a T cell expressing the CAR specific for tumor associated antigens.

The term "chimeric membrane protein" refers to an engineered membrane protein having an extracellular domain and intracellular domain derived from or capable of activating one or more signaling and/or receptor molecules. For example, the chimeric membrane protein described herein comprises a single chain variable fragment (scFv) directed against CD3 and an intracellular domain comprising a fragment of an intracellular domain of CD28 and 4-1BB.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for the ability to bind to antigen using the functional assays described herein.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

The term "derived from" refers to being generated, synthesized, or originating from a particular source, such that the derived matter is related to the source. The derived matter does not need to be identical to the particular source. In one embodiment, an antigen is derived from a protein. In another embodiment, a single-chain variable fragment is derived from a monoclonal antibody.

The terms "electroporate," "electroporation," "electroporated" refer to the process by which an electrical field is applied to a cell plasma membrane to increase its permeability. A pulse of a specific duration and shape is applied to the cell membrane of a cell to introduce nucleic acids into the cell.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

As used herein, the terms "expand," and "expansion" refer to the proliferation or multiplication of cells, such as T cells.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentivirus es, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequences derived from non-human immunoglobulins. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

The phrases "an immunologically effective amount", "an anti-immune response effective amount", "an immune response-inhibiting effective amount", or "therapeutic amount" refer to the amount of the composition of the present invention to be administered to a subject which amount is determined by a physician, optionally in consultation with a scientist, in consideration of individual differences in age, weight, immune response, type of disease/condition, and the health of the subject (patient) so that the desired result is obtained in the subject.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases arc used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly arc referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "signal transduction pathway" refers to the biochemical relationship between a variety of signal transduction molecules that play a role in the transmission of a signal from one region of a cell to another region of a cell. The phrase "cell surface receptor" includes molecules and complexes of molecules capable of receiving a signal and transmitting signal across the plasma membrane of a cell. An example of a "cell surface receptor" is human CD3 or CD28.

"Single chain antibodies" refer to antibodies formed by recombinant DNA techniques in which immunoglobulin heavy and light chain fragments are linked to the Fv region via an engineered span of amino acids. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 334: 54454; Skerra et al. (1988) Science 242:1038-1041.

By the term "specifically binds," as used herein, is meant an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class 1 molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "target site" or "target sequence" refers to a genomic nucleic acid sequence that defines a region of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha (a) and beta (β) chain, although in some cells the TCR consists of gamma and delta (γ/δ) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduccd with exogenous nucleic acid. The cell includes the primary subject cell and its progeny.

The phrase "under transcriptional control" or "operatively linked" as used herein means that the promoter is in the correct location and orientation in relation to a polynucicotide to control the initiation of transcription by RNA polymerasc and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention includes a method for expanding a population of electroporated T cells. The method includes electroporating a population of cells, such as peripheral blood mononuclear, comprising T cells with mRNA encoding a chimeric membrane protein, wherein the mRNA is introduced into at least one of the cells in the population and expressed on the surface of the cells. In one embodiment, the chimeric membrane protein comprises an antigen binding domain that binds to a molecule, such as TCR/CD3, and an intracellular domain of a co-stimulatory molecule In another embodiment, the electroporated population is cultured, wherein the T cells contained therein expand at least 10 fold. Accordingly, the present invention allows for expansion of T cells from a population of cells and preparation of the cells for therapeutic applications, such as adoptive cell transfer.

Methods

In one aspect, the invention includes a method of expanding a population of T cells where the method comprises the steps of electroporating a population of cells, such as peripheral blood mononuclear cells, comprising T cells with mRNA encoding a chimeric membrane protein. The chimeric membrane protein comprises an extracellular domain comprising an antigen binding domain comprising an antibody or fragment thereof that binds to a molecule, such as TCR/CD3, and an intracellular domain comprising a fragment of an intracellular domain of CD28 and 4-1BB. The mRNA is introduced into at least one of the cells in the population and expressed on the surface of the cells, and the electroporated population of cells are cultured, wherein the T cells contained therein expand at least 10 fold.

In another aspect, the invention includes a method for expanding a population of electroporated T cell where the method comprises the steps of electroporating a population of cells comprising T cells with mRNA encoding a chimeric membrane protein. The chimeric membrane protein comprises a single chain variable fragment (scFv) directed against CD3 and an intracellular domain comprising a fragment of an intracellular domain of CD28 and 4-1BB. The mRNA is introduced into at least one of the cells in the population and expressed on the surface of the cells. The electroporated population of cells is cultured, wherein the T cells contained therein expand at least 10 fold.

In one embodiment, the cells are selected from the group consisting of peripheral blood mononuclear cells, cord blood cells, a purified population of T cells, and a T cell line.

In another embodiment, the method describe herein further comprises electroporating a mRNA encoding an agent into the expanded population of T cells, such as co-electroporating the nucleic acid encoding the agent with the nucleic acid encoding the chimeric membrane protein.

In yet another embodiment, the method described herein further comprises stimulating the expanded population of T cells with at least one molecule or cytokine selected from the group consisting of CD27, CD28, CD83, CD86, CD127, 4-1BBL, IL21, TL15, TL-7, PD1-CD28 and PD1.

In still another embodiment, the method described herein further comprises cryopreserving the cultured T cells.

Introduction of Nucleic Acids

Methods of introducing nucleic acids into a cell include physical, biological and chemical methods. Physical methods for introducing a polynucleotide, such as RNA, into a host cell include calcium phosphate precipitation, lipofection, particle bombardment, microinjection, electroporation, and the like. RNA can be introduced into target cells using commercially available methods which include electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany). RNA can also be introduced into cells using cationic liposome mediated transfection using lipofection, using polymer encapsulation, using peptide mediated transfection, or using biolistic particle delivery systems such as "gene guns" (see, for example, Nishikawa, et al. Hum Gene Ther., 12(8):861-70 (2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

RNA

In one embodiment, RNA is introduced into target cells. Tn another embodiment, the RNA is mRNA that comprises in vitro transcribed RNA or synthetic RNA. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is a chimeric membrane protein. By way of example, the template encodes an antibody, a fragment of an antibody or a portion of an antibody. By way of another example, the template comprises an extracellular domain comprising a single chain variable domain of an antibody, such as anti-CD3, and an intracellular domain of a co-stimulatory molecule. In one embodiment, the template for the RNA chimeric membrane protein encodes a chimeric membrane protein comprising an extracellular domain comprising an antigen binding domain comprising an antibody or fragment thereof to a molecule, and an intracellular domain comprising a fragment of an intracellular domain of CD28 and 4-1BB.

PCR can be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as *E. coli* polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

In some embodiments, the mRNA encoding a chimeric membrane protein is electroporated into the cells. In one embodiment, the mRNA encoding a chimeric membrane protein is in vitro transcribed mRNA.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the chimeric receptor mRNAs with different structures and combination of their domains. For example, varying of different intracellular effector/costimulator domains on multiple chimeric receptors in the same cell allows determination of the structure of the receptor combinations which assess the highest level of cytotoxicity against multi-antigenic targets, and at the same time lowest cytotoxicity toward normal cells.

One advantage of RNA transfection methods of the invention is that RNA transfection is essentially transient and a vector-free. A RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. Tt is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct can be delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Sources of T Cells

Prior to expansion, a source of T cells is obtained from a subject. Non-limiting examples of subjects include humans, dogs, cats, mice, rats, and transgenic species thereof. Preferably, the subject is a human. T cells can be obtained from a number of sources, including peripheral blood mononuclear cells, bone marrow, lymph node tissue, spleen tissue, umbilical cord, and tumors. In certain embodiments, any number of T cell lines available in the art, may be used. In certain embodiments, T cells can be obtained from a unit of blood collected from a subject using any number of techniques known to the skilled artisan, such as Ficoll separation. In one embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells arc isolated from peripheral blood by lysing the red blood cells and depleting the monocytes, for example, by centrifugation through a PERCOLL™ gradient. Alternatively, T cells can be isolated from umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19 and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells arc mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In one embodiment, the population of cells may include peripheral blood mononuclear cells, cord blood cells, a purified population of T cells, and a T cell line. In another embodiment, the population of cells to be electroporated comprises peripheral blood mononuclear cells. In yet another embodiment, the population of cells to be electroporated comprises purified T cells.

Chimeric Membrane Protein

The chimeric membrane protein of the invention comprises an extracellular and intracellular domain. The extracellular domain comprises a target-specific binding element, such as an antibody. In one embodiment, the extracellular domain of the chimeric membrane protein targets a molecule on a T cell that includes but is not limited to TCR, CD3, CD28, and the like.

Extracellular Domain

The present invention includes an extracellular domain comprising an antigen binding domain comprising an antibody or fragment thereof directed against a molecule on T cells. The molecule can include any molecule that co-stimulates T cells, such as, but not limited to, TCR, CD3, CD28, or a combination thereof. In one embodiment, the extracellular domain can include an antigen binding domain comprising the CD3 binding domain of an anti-CD3 antibody, an anti-TCR antibody, anti-CD28 antibody, or a combination thereof.

In another embodiment, the extracellular domain can include any fragment of an antibody that binds to antigen including, but not limited to, the antigen binding domain of a synthetic antibody, human antibody, humanized antibody, single domain antibody, single chain variable fragments, and fragments thereof. In some instances, it is beneficial for the extracellular domain to be derived from the same species in which the chimeric membrane protein will ultimately be used in. For example, for use in humans, it may be beneficial for the extracellular domain of the chimeric membrane protein to comprise a human antibody or fragment thereof. Thus, in one embodiment, the extracellular domain comprises a human antibody or a fragment thereof.

In one embodiment, the antibody is a synthetic antibody, human antibody, humanized antibody, single domain antibody, single chain variable fragment, and antigen-binding fragments thereof.

Intracellular Domain

The intracellular domain or cytoplasmic domain comprises a costimulatory signaling region. The costimulatory signaling region refers to an intracellular domain of a costimulatory molecule. Costimulatory molecules are cell surface molecules other than antigen receptors or their ligands that are required for an efficient response of lymphocytes to antigen.

The cytoplasmic domain or the intracellular signaling domain of the chimeric membrane protein is responsible for activation of at least one of effector functions of the T cell. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Nonlimiting examples of intracellular signaling domains for use in the chimeric membrane protein include any fragment of the intracellular domain of CD28, 4-1BB, T cell receptor (TCR), co-stimulatory molecules, any derivative or variant of these sequences, any synthetic sequence that has the same functional capability, and any combination thereof.

Other Domains of the Chimeric Membrane Protein

Between the extracellular domain and the transmembrane domain of the chimeric membrane protein, or between the cytoplasmic domain and the transmembrane domain of the chimeric membrane protein, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

In some embodiments, the chimeric membrane protein further comprises a transmembrane domain. In some embodiment, the chimeric membrane protein further comprises a hinge domain. In one embodiment, the mRNA encoding the chimeric membrane protein further comprises a transmembrane and hinge domain, such as a CD28 transmembrane domain and a CD8-alpha hinge domain.

Human Antibodies

For in vivo use of antibodies in humans, it may be preferable to use human antibodies. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO98/16654, WO 96/34096, WO 96/33735, and WO 91/10741; each of which is incorporated herein by reference in its entirety. A human antibody can also be an antibody wherein the heavy and light chains arc encoded by a nucleotide sequence derived from one or more sources of human DNA.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Antibodies directed against the target of choice can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lonberg and Huszar (Int. Rev. Immunol., 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al., Proc. Natl. Acad. Sci. USA, 90:2551 (1993); Jakobovits et al., Nature, 362:255-258 (1993); Bruggermann et al., Year in Immunol., 7:33 (1993); and Duchosal et al., Nature, 355:258 (1992).

Human antibodies can also be derived from phage-display libraries (Hoogenboom et al., J. Mol. Biol., 227:381 (1991); Marks et al., J. Mol. Biol., 222:581-597 (1991); Vaughan et al., Nature Biotech., 14:309 (1996)). Phage display technology (McCafferty et al., Nature, 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially following the techniques described by Marks et al., J. Mol. Biol., 222:581-597 (1991), or Griffith et al., EMBO J., 12:725-734 (1993). See, also, U.S. Pat. Nos. 5,565,332 and 5,573,905, each of which is incorporated herein by reference in its entirety.

Human antibodies may also be generated by in vitro activated B cells (see, U.S. Pat. Nos. 5,567,610 and 5,229,275, each of which is incorporated herein by reference in its entirety). Human antibodies may also be generated in vitro using hybridoma techniques such as, but not limited to, that described by Roder et al. (Methods Enzymol., 121:140-167 (1986)).

Humanized Antibodies

Alternatively, in some embodiments, a non-human antibody is humanized, where specific sequences or regions of the antibody arc modified to increase similarity to an antibody naturally produced in a human. In one embodiment, the antigen binding domain is humanized.

A "humanized" antibody retains a similar antigenic specificity as the original antibody. However, using certain methods of humanization, the affinity and/or specificity of binding of the antibody for human CD3 antigen may be increased using methods of "directed evolution," as described by Wu et al., J. Mol. Biol., 294:151 (1999), the contents of which are incorporated herein by reference herein in their entirety.

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some FR residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

Antibodies can be humanized with retention of high affinity for the target antigen and other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and arc familiar to those skilled in the art. Computer programs arc available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. Tn general, the CDR residues arc directly and most substantially involved in influencing antigen binding.

Expansion of T Cells

In one embodiment, the invention includes a T cell comprising an electroporated mRNA encoding a chimeric membrane protein comprising a single chain variable fragment (scFv) directed against CD3 and an intracellular domain comprising a fragment of an intracellular domain of CD28 and 4-1BB. The invention also includes a population of electroporated or expanded T cells comprising an electroporated mRNA encoding a chimeric membrane protein comprising an extracellular domain comprising an antigen binding domain comprising an antibody or fragment thereof to a molecule, and an intracellular domain comprising a fragment of an intracellular domain of CD28 and 4-1BB. Tn another embodiment, the mRNA is introduced into at least one of the population of cells and expressed on the surface of the cells.

In one embodiment, the source of the T cells to be electroporated and expanded is peripheral blood mononuclear cells.

Generally, the T cells are expanded by contact with a surface having attached thereto an agent that stimulates a CD3/TCR complex associated signal and a ligand that stimulates a co-stimulatory molecule on the surface of the T cells. The present invention comprises a method of expanding a population of electroporated T cells comprising culturing the electroporated population, wherein the electroporated T cells contained within the population expand at least 10 fold. In one embodiment, at least one cell in the population of cells expresses CD3. Not being held to any particular theory, the cells that express CD3 may come into contact and bind with the chimeric membrane protein that is expressed on the surface of the electroporated cells. At least one cell expressing the chimeric membrane protein may interact with another cell expressing CD3. This may stimulate expansion of the electroporated T cells.

As demonstrated by the data disclosed herein, expanding the electroporated T cells by the methods disclosed herein can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the T cells expand in the range of about 20 fold to about 50 fold.

Following culturing, the T cells can be incubated in cell medium in a culture apparatus for a period of time or until the cells reach confluency or high cell density for optimal passage before passing the cells to another culture apparatus. The culturing apparatus can be any culture apparatus commonly used for culturing cells in vitro. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately or cryopreserved to be stored for use at a later time. In one embodiment, the method further comprises cryopreserving the cultured T cells.

The cells can be further expanded using a method described in U.S. Pat. No. 5,199,942 (incorporated herein by reference). Expansion, such as described in U.S. Pat. No. 5,199,942 can be in addition to other methods of expansion described herein. Briefly, ex vivo culture and expansion of T cells comprises the addition to the cellular growth factors, such as those described in U.S. Pat. No. 5,199,942, or other factors, such as flt3-L, IL-1, IL-2, IL-3 and c-kit ligand, for example as those described in Dudley et al., J. Immunol., 26(4):332-342, 2003, for a Rapid Expansion Protocol (REP).

In one aspect, the method of expanding the T cells can further comprise isolating the T cells and a subsequent electroporation followed by culturing.

The culturing step as described herein (contact with agents as described herein) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they arc referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

In one embodiment, the cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells arc maintained under conditions necessary to support growth, for example, an appropriate temperature (e.g., 37° C.) and atmosphere (e.g., air plus 5% $CO_2$).

The medium used to culture the T cells may include an agent that can co-stimulate the T cells. For example, an agent that can stimulate CD3 is an antibody to CD3, and an agent that can stimulate CD28 is an antibody to CD28. This is because, as demonstrated by the data disclosed herein, a cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the T cells expand in the range of about 20 fold to about 50 fold, or more by culturing the electroporated population.

In another embodiment, the method of expanding the T cells can further comprise isolating the expanded T cells for further applications. In yet another embodiment, the method of expanding can further comprise a subsequent electroporation of the expanded T cells followed by culturing. The subsequent electroporation may include electroporating a mRNA encoding an agent into the expanded population of T cells, wherein the agent further stimulates the T cell. The agent may stimulate the T cell, such as by stimulating further expansion, effector function, or another T cell function. In one embodiment, the agent mRNA is co-electroporated with the chimeric membrane protein mRNA. In another embodiment, the agent mRNA is electroporated after culturing the electroporated population.

In another embodiment, the method further comprises stimulating the expanded population of T cells with at least one co-stimulatory molecule selected from the group consisting of CD3, CD27, CD28, CD83, CD86, CD127, 4-IBBL and PD1.

Therapy

The T cells described herein may be included in a composition for therapy. The composition may include a pharmaceutical composition and further include a pharmaceutically acceptable carrier. A therapeutically effective amount of the pharmaceutical composition comprising the T cells may be administered.

In one aspect, the invention includes a method for stimulating a T cell-mediated immune response to a target cell or tissue in a subject comprising administering to a subject an effective amount of a T cell comprising with mRNA encoding a chimeric membrane protein comprising single chain variable fragment (scFv) directed against CD3 and an intracellular domain comprising a fragment of an intracellular domain of CD28 and 4-1BB, wherein at least one of the cells in the population expresses the chimeric membrane protein. The T cells may be administered to induce lysis of the target cell or tissue, such as where the induced lysis is antibody-dependent cell-mediated cytotoxicity (ADCC).

In one embodiment, the invention includes a method for adoptive cell transfer therapy. The method comprises administering an expanded population of cells comprising T cells to a subject in need thereof to prevent or treat a condition that is adverse to the subject. In this embodiment, the expanded population of cells is expanded according to a method comprising electroporating a population of cells comprising T cells with mRNA encoding a chimeric membrane protein comprising single chain variable fragment (scFv) directed against CD3 and an intracellular domain comprising a fragment of an intracellular domain of CD28 and 4-1BB, wherein at least one of the cells in the population express the chimeric membrane protein; and culturing the cell population, wherein the T cells contained therein expand at least 10 fold.

In another embodiment, there is provided a method of treating a disease or condition associated with enhanced immunity in a subject comprises administering an expanded population of cells comprising T cells to a subject in need thereof. The expanded population of cells has been expanded according to a method comprising electroporating a population of cells comprising T cells with mRNA encoding a chimeric membrane protein comprising single chain variable fragment (scFv) directed against CD3 and an intracellular domain comprising a fragment of an intracellular domain of CD28 and 4-1BB, wherein at lease one of the cells in the population expresses the chimeric membrane protein; and culturing the population of cells, wherein the T cells contained therein expand at least 10 fold.

The expanded T cells generated as described herein are uniform and possess T cell function. Further, the expanded T cells can be administered to a mammal, preferably a human, to suppress an immune reaction, such as those common to autoimmune diseases such as diabetes, psoriasis, rheumatoid arthritis, multiple sclerosis, GVHD, enhancing allograft tolerance induction, transplant rejection, and the like. In addition, the cells of the present invention can be used for the treatment of any condition in which a diminished or otherwise inhibited immune response, especially a cell-mediated immune response, is desirable to treat or alleviate the disease.

The expanded T cells generated as described herein can also be used to treat autoimmune diseases. Examples of autoimmune disease include but are not limited to, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/giant cell arteritis, ulcerative colitis, uveitis, vitiligo and Wegener's granulomatosis.

The expanded T cells generated as described herein can also be used to treat inflammatory disorders. Examples of inflammatory disorders include but are not limited to, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

In another embodiment, the T cells described herein may be used for the manufacture of a medicament for the treatment of an immune response in a subject in need thereof.

The cells of the present invention can be administered to an animal, preferably a mammal, even more preferably a human, to treat a cancer. In addition, the cells of the present invention can be used for the treatment of any condition related to a cancer, especially a cell-mediated immune response against a tumor cell(s), where it is desirable to treat or alleviate the disease. Examples of cancers include but are not limited breast cancer, prostate cancer, ovarian cancer, cervical cancer, skin cancer, pancreatic cancer, colorectal cancer, renal cancer, liver cancer, brain cancer, lymphoma, leukemia, lung cancer, thyroid cancer, and the like.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

The cells of the invention to be administered may be autologous, allogeniec or xenogenic with respect to the subject undergoing therapy.

The administration of the cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

The cells described herein can also be administered using any number of matrices. The present invention utilizes such matrices within the novel context of acting as an artificial lymphoid organ to support, maintain, or modulate the immune system, typically through modulation of T cells. Accordingly, the present invention can utilize those matrix compositions and formulations which have demonstrated utility in tissue engineering. Accordingly, the type of matrix that may be used in the compositions, devices and methods of the invention is virtually limitless and may include both biological and synthetic matrices. In one particular example, the compositions and devices set forth by U.S. Pat. Nos. 5,980,889; 5,913,998; 5,902,745; 5,843,069; 5,787,900; or 5,626,561 arc utilized, as such these patents arc incorporated herein by reference in their entirety. Matrices comprise features commonly associated with being biocompatible when administered to a mammalian host. Matrices may be formed from natural and/or synthetic materials. The matrices may be non-biodegradable in instances where it is desirable to leave permanent structures or removable structures in the body of an animal, such as an implant; or biodegradable. The matrices may take the form of sponges, implants, tubes, telfa pads, fibers, hollow fibers, lyophilized components, gels, powders, porous compositions, or nanoparticles. In addition, matrices can be designed to allow for sustained release of seeded cells or produced cytokine or other active agent. In certain embodiments, the matrix of the present invention is flexible and elastic, and may be described as a semisolid scaffold that is permeable to substances such as inorganic salts, aqueous fluids and dissolved gaseous agents including oxygen.

A matrix is used herein as an example of a biocompatible substance. However, the current invention is not limited to matrices and thus, wherever the term matrix or matrices appears these terms should be read to include devices and other substances which allow for cellular retention or cellular traversal, are biocompatible, and are capable of allowing traversal of macromolecules either directly through the substance such that the substance itself is a semi-permeable membrane or used in conjunction with a particular semi-permeable substance.

Pharmaceutical Compositions

Pharmaceutical compositions of the present invention may comprise an expanded T cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

It can generally be stated that a pharmaceutical composition comprising the expanded T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 ml to 400 ml. In certain embodiments, T cells are activated from blood draws of 20 ml, 30 ml, 40 ml, 50 ml, 60 ml, 70 ml, 80 ml, 90 ml, or 100 ml. Not to be bound by theory, using this multiple blood draw/multiple reinfusion protocol, may select out certain populations of T cells.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

Experimental Examples

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The Materials and Methods used in the performance of the experiments disclosed herein are now described.

Construction of in vitro transcription (IVT) mRNA vectors. All genes were synthesized and/or amplified and assembled by PCR using publically available sequence information. The PCR products were subcloned into a pGEM.64A based vector by replacing GFP of pGEM-GFP.64A to produce a pGEM.64A based IVT vector with publically available sequencing information.

RNA in vitro transcription (IVT). An in vitro transcription kit, such as mMESSAGE mMACHINE® T7 Ultra (Ambion, Inc), was used to generate IVT RNA. The IVT RNA products were purified using a RNA purification protocol, such as RNeasy Mini Kit (Qiagen, Inc., Valencia, CA). Purified RNA was eluted in RNase-free water at about 1-2 mg/ml.

RNA electroporation of T cells. PBMCs or expanded T cells were subjected to electroporation were washed three times with OPTI-MEM (Invitrogcn) and re-suspended in OPTI-MEM at the final concentration of 1-3×$10^8$/ml. Subsequently, 0.1 ml of the cells was mixed with 10 ug IVT RNA (or as indicated) and electroporated in a 2-mm cuvette using an clectroporator, such as BTX EM830 (Harvard Apparatus BTX, Holliston, MA, USA).

T cell stimulation and expansion. PBMCs were electroporated with RNA encoding anti-CD3 scFv-28BB and cultured in R10 medium supplemented with 300 u/ml 1L-2. Fresh medium with 1L-2 was added to the culture every other day starting day 3 after electroporation. T cell phenotype and function were tested day 9 post stimulation. CD3/CD28 bead stimulated T cells, or T cells expanded by adding OKT3 antibody to PBMCs were used as controls.

CAR detection on electroporated T Cells. Cells were washed and suspended in FACs buffer (PBS plus 0.1% sodium azide and 0.4% BSA). Biotin-labeled polyclonal goat anti-mouse F(ab)2 antibodies (for murine scFv) or anti-human anti-F(ab)2 (for human scFv) (Jackson Immunoresearch, West Grove, PA) were added to the cells and incubated at 4° C. for 25 minutes then washed twice. The cells were then stained with phycoerythrin-labeled streptavidin (BD Pharmingen, San Diego, CA).

ELISA and Luminex assays. Target cells, different tumor cell lines expressing CD19, were washed and suspended at $10^6$ cells/mL in R10 media. One hundred thousand cells of each target cell type were added to duplicate wells of a 96 well round bottom plate (Corning). Effector T cell cultures, CD19 CAR RNA electroporated T cell populations, were washed and suspended at $10^6$ cells/mL in R10. One hundred thousand effector T cells were combined with target cells in the indicated wells of the 96 well plate. In addition, wells containing T cells alone were prepared. The plates were incubated at 37° C. for 18 to 20 hours. After the incubation, supernatant was harvested and subjected to an ELISA assay using standard methods (Pierce, Rockford, IL).

CD107a staining. Cells were plated at an E:T of 1:1 ($10^5$ effectors:$10^5$ targets) in 160 µl of complete RPMI medium in a 96 well plate. 20 µl of phycoerythrin-labeled anti-CD107a antibody (BD Pharmingen, San Diego, CA) was added and the cells were incubated at 37° C. for 1 hour before adding Golgi Stop and incubating for another 2.5 hours. After 2.5 hours 10 µl FITC-anti-CD8 and APC-anti-CD3 was added and the cells were incubated at 37° C. for 30 min. After incubation, the samples were washed once with FACS buffer. Flow cytometry acquisition was performed with a BD FacsCalibur (BD Biosciences), and analysis was performed with FlowJo (Treestar Ashland, OR).

Luciferase based CTL assay. Nalm6-CBG (or Nalm6-CBG transduced with either PDL1 or HVEM) were generated and used in a modified version of a luciferase based cytotoxic T lymphocyte (CTL) assay as follows. Nalm6-CBG cells were washed and resuspended at 1×$10^5$ cells/ml in R10 medium, and 100 ul of CBG-labeled cells were incubated with different ratios of T cells (e.g. 30:1, 15:1, etc) overnight at 37° C. 100 ul of the mixture was transferred to a 96 well white luminometerplate, 100 ul of substrate was added and luminescence was immediately determined.

SEQ ID NO: 1

```
atggcactgcccgtgaccgccctcctcctgcccctcgcgctactcctgcacgccgccagaccccaggtgcagctgcagcagag

tggcgctgagctggcccgccccggcgcctccgtgaagatgtcctgcaaggctagtgggtataccttcaccaggtatactatgca

ctgggtgaagcagcgtccggggcaggggctcgagtggatcggctacatcaatccctcccgcggctacaccaattacaaccaga

agttcaaggataaggccacgctgaccacagacaagagtagctccacggcctacatgcagttatcaagtctgacctctgaggact

ccgctgtgtactattgtgcgaggtactacgacgaccactactgtctggactactggggccaaggcacaaccctgactgtaagttcc

tccggcggcgggggtccggcggcggcggctccggcgggggggtagtatcgtgctgacacagagtcccgcaatcatgtcc

gcaagccccggagagaaggtgaccatgacgtgtagtgcttccagctccgtgtcctatatgaactggtaccagcagaaatccggg
```

acttcccccaagagatggatctacgacaccagtaagctggccagtggcgtgcctgcacacttccgcggcagtggctccggcact
agttacagtctcaccatctccgggatggaagctgaggacgccgctacctactactgccagcagtggagctcgaacccattcacct
tcggttcggggaccaagctcgagatcaacagggcggccgccaccacgacgccagcgccgcgaccaccaacaccggcgccc
accatcgcgtcgcagcccctgtccctgcgcccagaggcgtgccggccagcggcggggggcgcagtgcacacgagggggct
ggacttcgcctgtgatttttgggtgctggtggtggttggtggagtcctggcttgctatagcttgctagtaacagtggcctttattattttc
tgggtgaggagtaagaggagcaggctcctgcacagtgactacatgaacatgactccccgccgccccgggcccacccgcaag
cattaccagccctatgccccaccacgcgacttcgcagcctatcgctccaaacggggcagaaagaaactcctgtatatattcaaac
aaccatttatgagaccagtacaaactactcaagaggaagatggctgtagctgccgatttccagaagaagaagaaggaggatgtg
aactgtaa

SEQ ID NO: 2 atggcactgcccgtgaccgccctcctcctgcccctcgcgctactcctgcacgccgccagacccgacgtgcagctcgtgcagtcc
ggggccgaggtcaagaagccaggcgcctccgtgaaagtgtcgtgcaaggcttccgggtacacgttcacgaggtacacgatgc
actgggtgcggcaggcccccggccagggcctggagtggatcggctacatcaatccctctcgcggctacacaaattacgccgac
tccgtgaaaggccggttcaccattactaccgacaagtccaccagcactgcctatatggagctgtccagtctccgcagcgaggata
cggccacgtactactgtgcccgatactacgacgaccactactgcctggactactgggggcagggaaccaccgtgacagtgtctt
ccggggaagggaccagcactggctcgggcggctccgggggttccgggggtgccgacgatatccagatgacccaaagtccca
gctcgctgagcgccagtgtcggcgatcgcgtgaccatcacctgccgcgcgtctcagtctgtgtcctacatgaactggtaccagca
aaagcccggtaaggcccccaagcgctggatctacgacaccagcaaagtcgcctcgggcgtccccgcccggttcagcgggtcc
gggtccgggacagattactcgctcacgatcaactcgctggaggcggaagacgccgcaacttattattgccagcagtggagttcc
aaccctctgaccttcgggggtggcacgaaggtggaaatcaaggcggccgccaccacgacgccagcgccgcgaccaccaac
accggcgcccaccatcgcgtcgcagcccctgtccctgcgcccagaggcgtgccggccagcggcggggggcgcagtgcaca
cgagggggctggacttcgcctgtgatttttgggtgctggtggtggttggtggagtcctggcttgctatagcttgctagtaacagtgg
cctttattattttctgggtgaggagtaagaggagcaggctcctgcacagtgactacatgaacatgactccccgccgccccgggcc
cacccgcaagcattaccagccctatgccccaccacgcgacttcgcagcctatcgctccaaacggggcagaaagaaactcctgt
atatattcaaacaaccatttatgagaccagtacaaactactcaagaggaagatggctgtagctgccgatttccagaagaagaaga
aggaggatgtgaactgtaa

SEQ ID NO: 3 atg gcg cgc ggc ctc cag ctt ctg ctc ctg agc tgc gcc tac agc ctg gct ccc gcg acg ccg gag gtg
aag gtg gct tgc tcc gaa gat gtg gac ttg ccc tgc acc gcc ccc tgg gat ccg cag gtt ccc tac acg
gtc tcc tgg gtc aag tta ttg gag ggt ggt gaa gag agg atg gag aca ccc cag gaa gac cac ctc agg
gga cag cac tat cat cag aag ggg caa aat ggt tct ttc gac gcc ccc agc cgc cat gaa agg ccc tat
tcc ctg aag atc cga aac act acc agc tgc aac tcg ggg aca tac agg tgc act ctg cag gac ccg gat
ggg cag aga aac cta agt ggc aag gtg atc ttg aga gtg aca gga tgc cct gca cag cgt aaa gaa gag
act ttt aag aaa tac aga gcg gag att gtc ctg ctg ctg gct ctg gtt att ttc tac tta aca ctc atc
att ttc act tgt aag ttt gca cgg cta cag agt atc ttc cca gat ttt tct aaa gct ggc atg gaa cga
gct ttt ctc cca gtt acc tcc cca aat aag cat tta ggg cta gtg act cct cac aag aca gaa ctg gta
tga

SEQ ID NO: 4 atggatccccagtgcactatgggactgagtaacattctctttgtgatggccttcctgctctctggtgctgctcctctgaagattcaagc
ttatttcaatgagactgcagacctgccatgccaatttgcaaactctcaaaaccaaagcctgagtgagctagtagtattttggcagga
ccaggaaaacttggttctgaatgaggtatacttaggcaaagagaaatttgacagtgttcattccaagtatatgggccgcacaagtttt
gattcggacagttggaccctgagacttcacaatcttcagatcaaggacaagggcttgtatcaatgtatcatccatcacaaaaagcc
cacaggaatgattcgcatccaccagatgaattctgaactgtcagtgcttgctaacttcagtcaacctgaaatagtaccaatttctaat -continued ataacagaaaatgtgtacataaatttgacctgctcatctatacacggttacccagaacctaagaagatgagtgttttgctaagaacca agaattcaactatcgagtatgatggtgttatgcagaaatctcaagataatgtcacagaactgtacgacgtttccatcagcttgtctgtt tcattccctgatgttacgagcaatatgaccatcttctgtattctggaaactgacaagacgcggcttttatcttcacctttctctatagagc ttgaggaccctcagcctcccccagaccacattccttggattacagctgtacttccaacagttattatatgtgtgatggttttctgtctaa ttctatggaaatggaagaagaagaagcggcctcgcaactcttataaatgtggaaccaacacaatggagagggaagagagtgaa cagaccaagaaaagagaaaaaatccatatacctgaaagatctgatgaagcccagcgtgtttttaaaagttcgaagacatcttcatg cgacaaaagtgatacatgtttttaa

SEQ ID NO: 5 atggaatacgcctctgacgcttcactggaccccgaagccccgtggcctcccgcgccccgcgctcgcgcctgccgcgtactgcc ttgggccctggtcgcggggctgctgctgctgctgctgctcgctgccgcctgcgccgtcttcctcgcctgcccctgggccgtgtcc ggggctcgcgcctcgcccggctccgcggccagcccgagactccgcgagggtcccgagctttcgcccgacgatcccgccggc ctcttggacctgcggcagggcatgtttgcgcagctggtggcccaaaatgttctgctgatcgatgggcccctgagctggtacagtg acccaggcctggcaggcgtgtccctgacgggggcctgagctacaaagaggacacgaaggagctggtggtggccaaggct ggagtctactatgtcttctttcaactagagctgcggcgcgtggtggccggcgagggctcaggctccgtttcacttgcgctgcacct gcagccactgcgctctgctgctggggccgccgccctggctttgaccgtggacctgccacccgcctcctccgaggctcggaact cggccttcggtttccagggccgcttgctgcacctgagtgccggccagcgcctgggcgtccatcttcacactgaggccagggca cgccatgcctggcagcttacccagggcgccacagtcttgggactcttccgggtgacccccgaaatcccagccggactcccttca ccgaggtcggaataa

SEQ ID NO: 6 atgcagatcccacaggcgccctggccagtcgtctgggcggtgctacaactgggctggcggccaggatggttcttagactcccc agacaggccctggaacccccccaccttctccccagccctgctcgtggtgaccgaaggggacaacgccaccttcacctgcagct tctccaacacatcggagagcttcgtgctaaactggtaccgcatgagccccagcaaccagacggacaagctggccgccttcccc gaggaccgcagccagcccggccaggactgccgcttccgtgtcacacaactgcccaacgggcgtgacttccacatgagcgtgg tcagggcccggcgcaatgacagcggcacctacctctgtggggccatctccctggcccccaaggcgcagatcaaagagagcct gcgggcagagctcagggtgacagagagaagggcagaagtgcccacagcccaccccagcccctcacccaggccagccggc cagttccaaaccctggtgttttgggtgctggtggtggttggtggagtcctggcttgctatagcttgctagtaacagtggcctttattatt ttctgggtgaggagtaagaggagcaggctcctgcacagtgactacatgaacatgactccccgccgccccgggcccacccgca agcattaccagccctatgccccaccacgcgacttcgcagcctatcgctcctaa

SEQ ID NO: 7 atggccttaccagtgaccgccttgctcctgccgctggccttgctgctccacgccgccaggccggacatccagatgacacagact acatcctccctgtctgcctctctgggagacagagtcaccatcagttgcagggcaagtcaggacattagtaaatatttaaattggtat cagcagaaaccagatggaactgttaaactcctgatctaccatacatcaagattacactcaggagtcccatcaaggttcagtggca gtgggtctggaacagattattctctcaccattagcaacctggagcaagaagatattgccacttacttttgccaacagggtaatacgc ttccgtacacgttcggaggggggactaagttggaaataacaggtggcggtggctcgggcggtggtgggtcgggtggcggcgg atctgaggtgaaactgcaggagtcaggacctggcctggtggcgccctcacagagcctgtccgtcacatgcactgtctcaggggt ctcattacccgactatggtgtaagctggattcgccagcctccacgaaagggtctggagtggctgggagtaatatggggtagtgaa accacatactataattcagctctcaaatccagactgaccatcatcaaggacaactccaagagccaagttttcttaaaaatgaacagt ctgcaaactgatgacacagccatttactactgtgccaaacattattactacggtggtagctatgctatggactactggggtcaagga acctcagtcaccgtctcctcaaccacgacgccagcgccgcgaccaccaacaccggcgcccaccatcgcgtcgcagcccctgt ccctgcgcccagaggcgtgccggccagcggcgggggggcgcagtgcacacgagggggctggacttcgcctgtgatatctaca tctgggcgcccttggccgggacttgtggggtccttctcctgtcactggttatcaccctttactgcaaacggggcagaaagaaactc ctgtatatattcaaacaaccatttatgagaccagtacaaactactcaagaggaagatggctgtagctgccgatttccagaagaaga -continued

```
agaaggaggatgtgaactgagagtgaagttcagcaggagcgcagacgcccccgcgtaccagcagggccagaaccagctcta
taacgagctcaatctaggacgaagagaggagtacgatgttttggacaagagacgtggccgggaccctgagatgggggggaaag
ccgagaaggaagaaccctcaggaaggcctgtacaatgaactgcagaaagataagatggcggaggcctacagtgagattggga
tgaaaggcgagcgccggaggggcaaggggcacgatggcctttaccagggtctcagtacagccaccaaggacacctacgacg
cccttcacatgcaggccctgccccctcgctaa
```

The Results of the experiments disclosed herein are now described.

Figure 2:
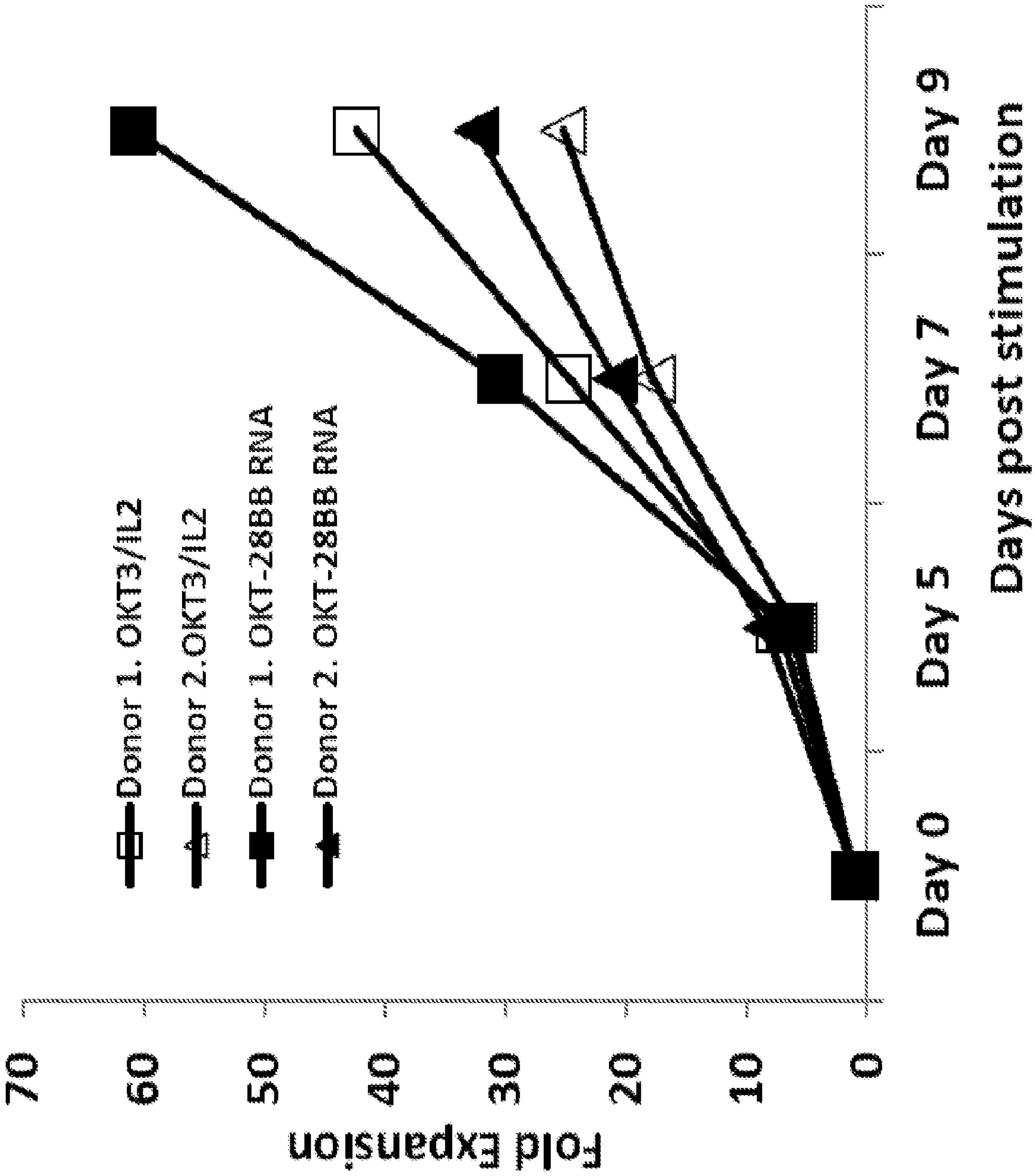
FIG. 2 is a graph showing the expansion of T cells stimulated by electroporation of OKT-28BB RNA.

T cell expansion with CD3 scFv-28BB RNA electroporated as efficient as T cells stimulated with anti-CD3 OKT3 antibody. Single chain variable fragment (scFv) domains from antibodies directed against CD3 (OKT3 or H5L1) were synthesized and/or amplified by PCR, linked to a CD8 transmembrane domain, CD28 and 4-1BB intracellular signaling domains, and subcloned into a pGEM.64A RNA based vector (FIG. 1). RNA was synthesized from the modified pGEM.64A constructs (OKT3-28BB RNA or H5L1 RNA) and electroporated into peripheral blood mononuclear cells (PBMCs). T cell expansion was assessed in the PBMC populations obtained from two normal PBMC donors. The PBMCs expanded after OKT3-28BB RNA electroporation were compared to PBMCs incubated with anti-CD3 OKT3 antibody. The results demonstrated that T cells expanded after OKT3-28BB RNA electroporation was as efficient as expansion of T cells after OKT3 antibody stimulation (FIG. 2).

Figure 3:
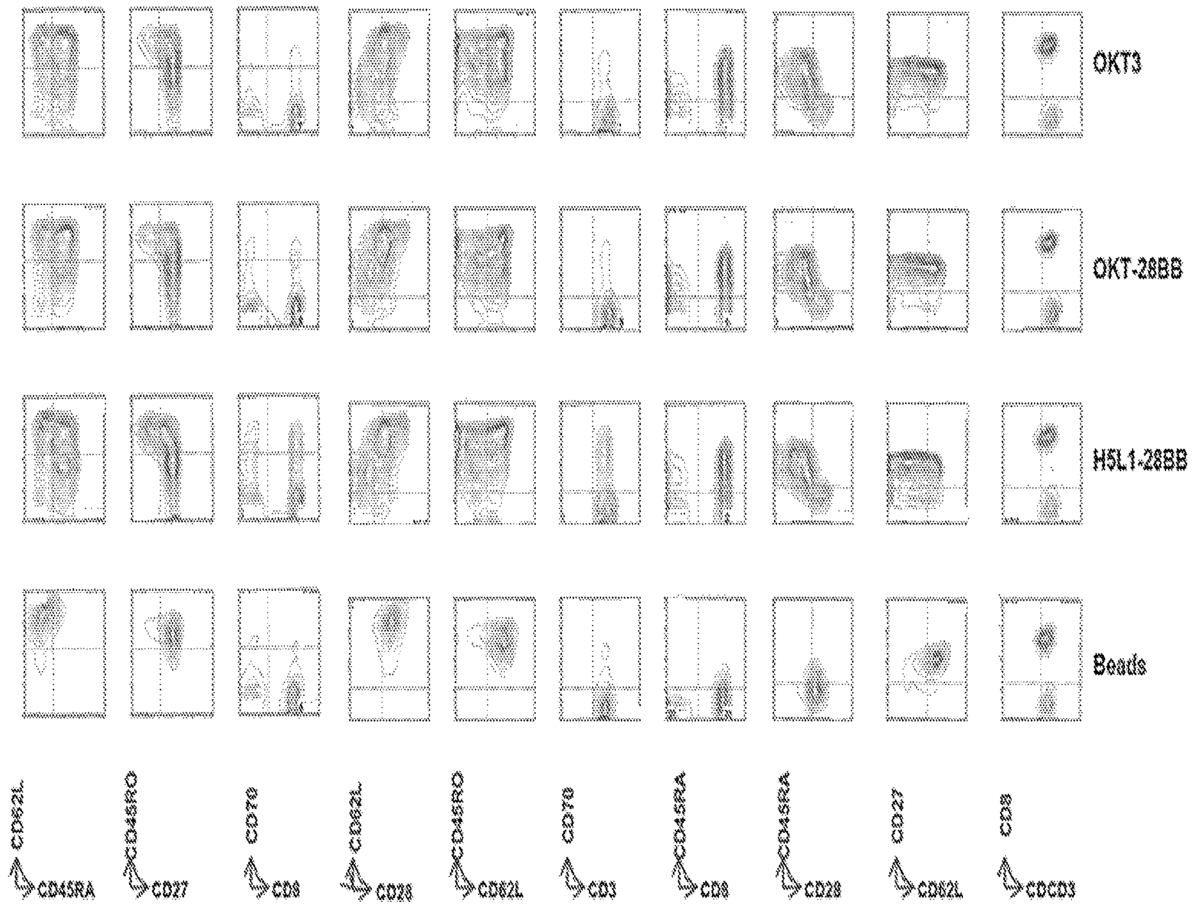
FIG. 3 is a panel of graphs showing the phenotype analysis of the expanded T cells. The phenotype of the T cells expanded by OKT-28BB or H5L1-28BB RNA electroporated T cells was compared with the phenotype of the T cells expanded by OKT3 stimulation (OKT3) or CD28/CD3 beads (Beads) stimulation 10 days after stimulation.

T cells expanded from CD3 scFv-28BB RNA electroporated PBMCs exhibited phenotypes similar to OKT3 antibody stimulated T cells and had superior effector function. The phenotype of T cells expanded by different methods, including stimulation of PBMCs with OKT3, purified T cells with anti-CD3/anti-CD28 coated beads (Beads), or electroporating PBMCs with either OKT-28BB RNA or H5L1-28BB RNA (, was assessed. The results demonstrated that the phenotype of T cells obtained by electroporation of PBMCs with RNA encoding OKT-28BB or H5L1-28BB was similar to that of T cells from PMBCs stimulated with OKT3 antibody, which included a large number of effector memory T cells (CD45RO+/CD62L−), while anti-CD3/anti-CD28 bead stimulated T cells exhibited a phenotype that was uniformly central memory phenotype (CD45RO+/Cd62L+) (FIG. 3).

Figure 4:
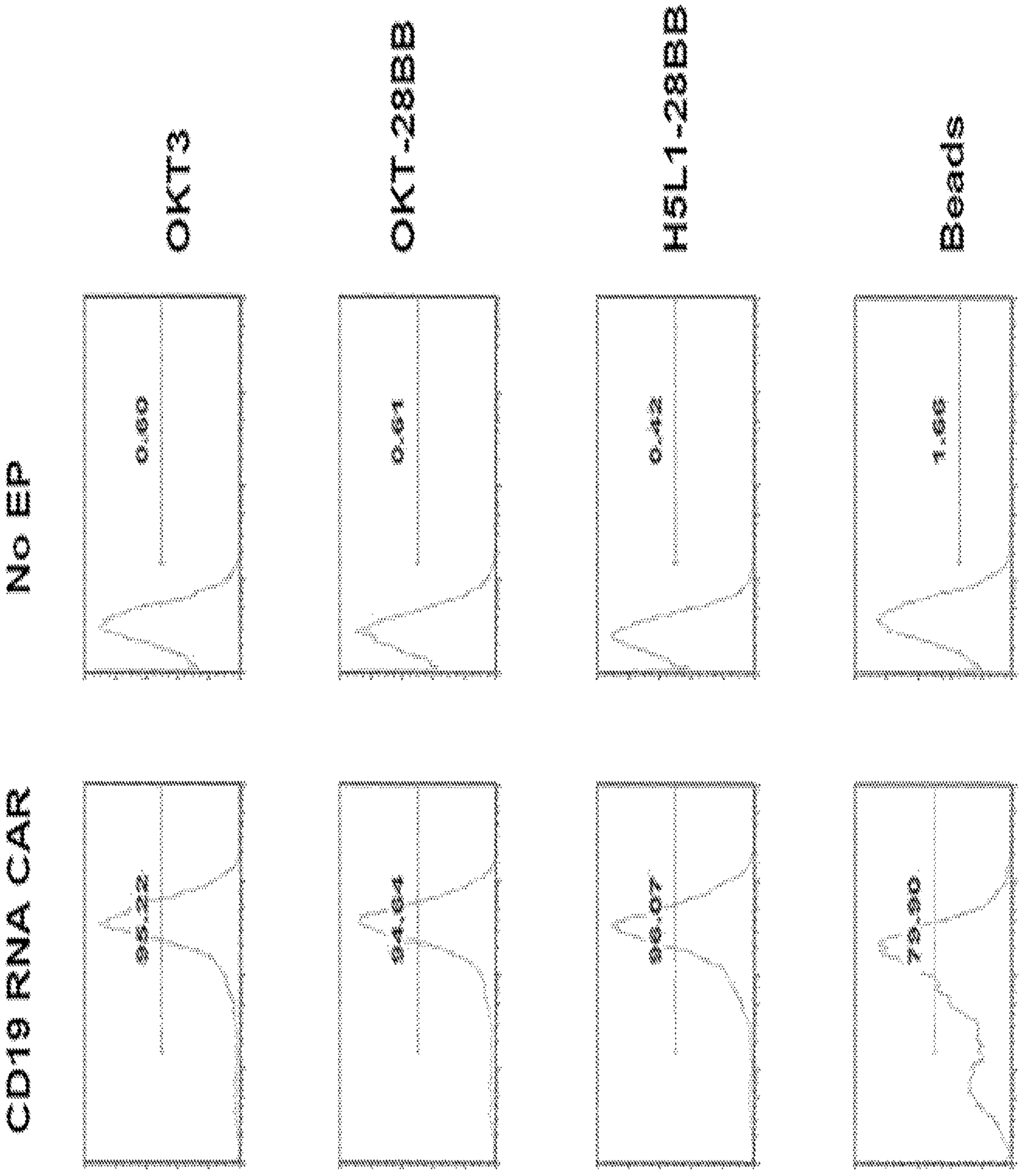
FIG. 4 is a panel of graphs highlighting the function of the expanded T cells. T cells were expanded for 10 days using different methods as indicated. OKT3: added OKT3 antibody directly to PBMCs (OKT3); OKT-28BB: electroporated PBMCs with OKT3-28BB; H5L1-28BB: electroporated PBMCs with H5L1-28BB; or Beads: added CD3/CD28 beads directly to PBMCs. All groups were electroporated with a CD19 chimeric antigen receptor (CAR) RNA to test T cell function by stimulating with CD19 positive tumor Nalm6. CD19 CAR expression of CD19 CAR RNA electroporated T cells was determined at 18 hr post RNA electroporation.
Figure 5A:
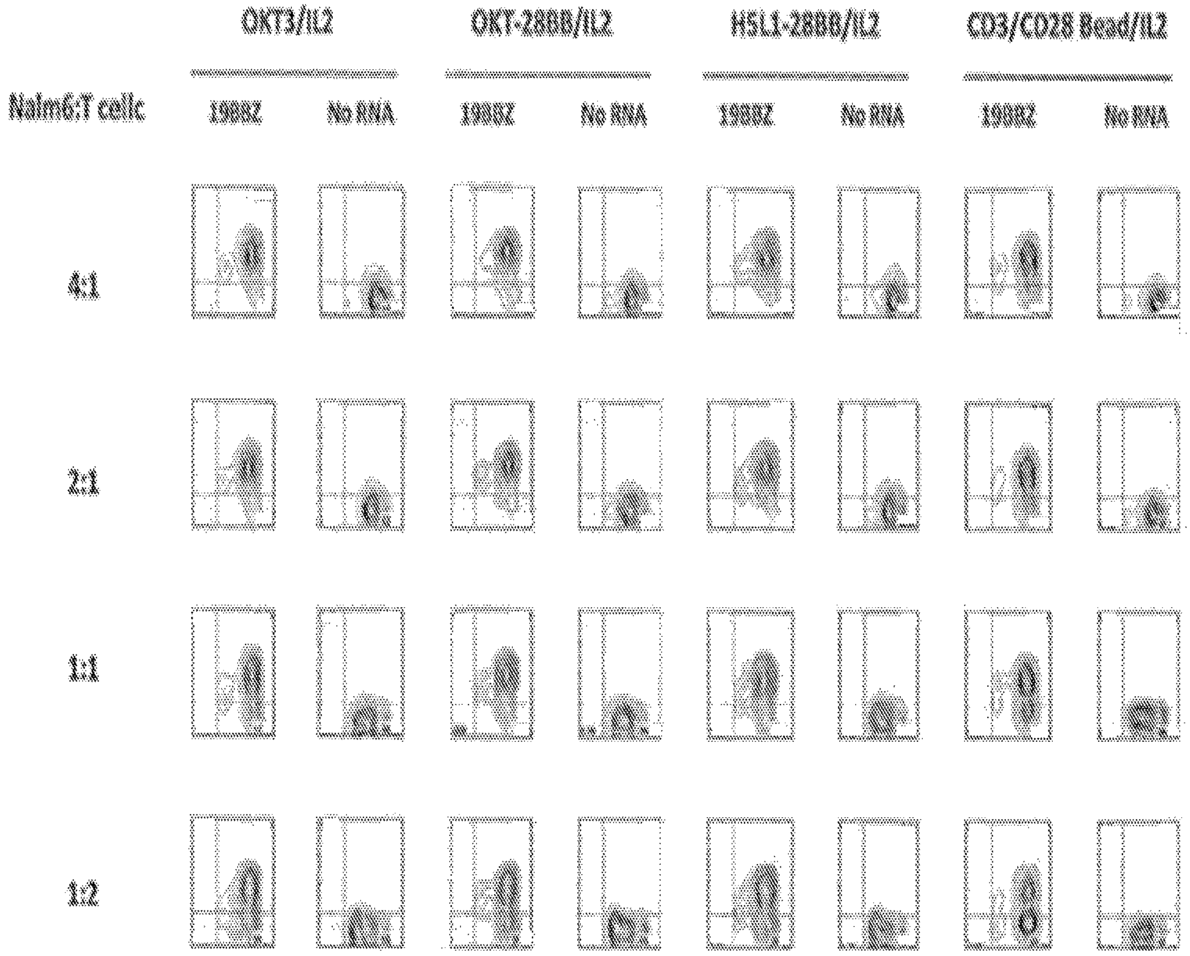
FIG. 5, comprising FIGS. 5A-B, further depict the function of expanded T cells electroporated with CD19 CAR RNA. The expanded cells were stimulated with Nalm6 at T cell:Nalm6 cell at different ratios (FIG. 5A). Percentages of CD107a positive T cells were plotted (FIG. 5B).
Figure 5B:
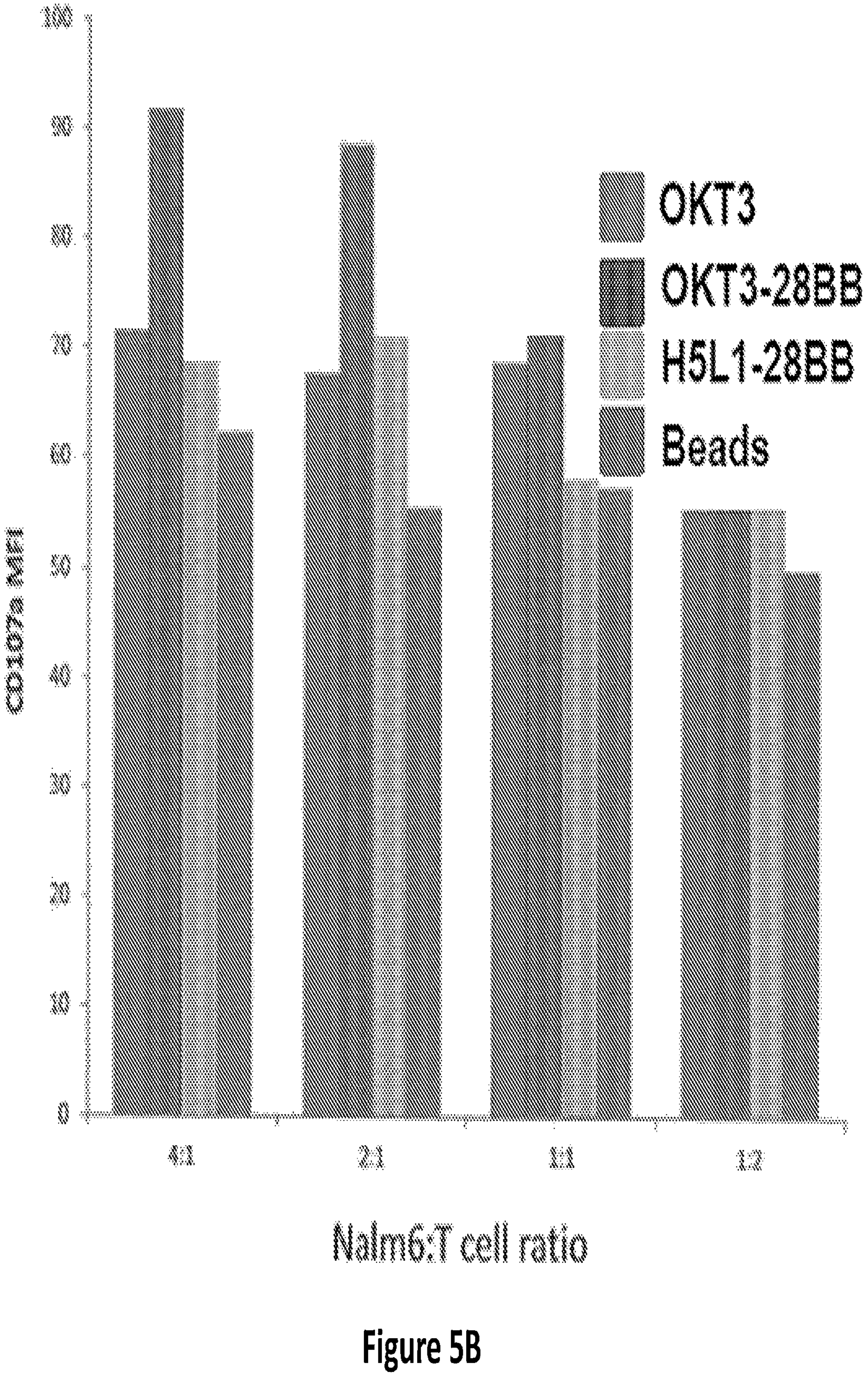

T cells were further assessed for functionality after electroporation with RNA encoding a CD19 CAR. Expression of the electroporated CD19 CAR RNA was similar in each of the T cell populations (FIG. 4) CD19 CAR RNA electroporated T cell populations obtained from OKT3 antibody stimulated PBMCs,OKT-28BB RNA electroporated PBMCs, H5L1-28BB RNA electroporated PBMCs, and anti-CD3/anti-CD28 bead stimulated PBMCs, were assessed for CD107a upregulation after co-incubating the T cells with a CD19 positive tumor cell line, Nalm6 (FIGS. 5A and 5B). The results demonstrated higher CD107a expression in OKT-28BB RNA electroporated T cells than T cells stimulated with OKT3 antibody or anti-CD3/anti-CD28 beads. T cells obtained from OKT-28BB RNA electroporated PBMCs have more robust functionality, assessed by anti-tumor activity, than both OKT3 antibody and CD3/CD28 beads stimulated T cells.

Figure 6:
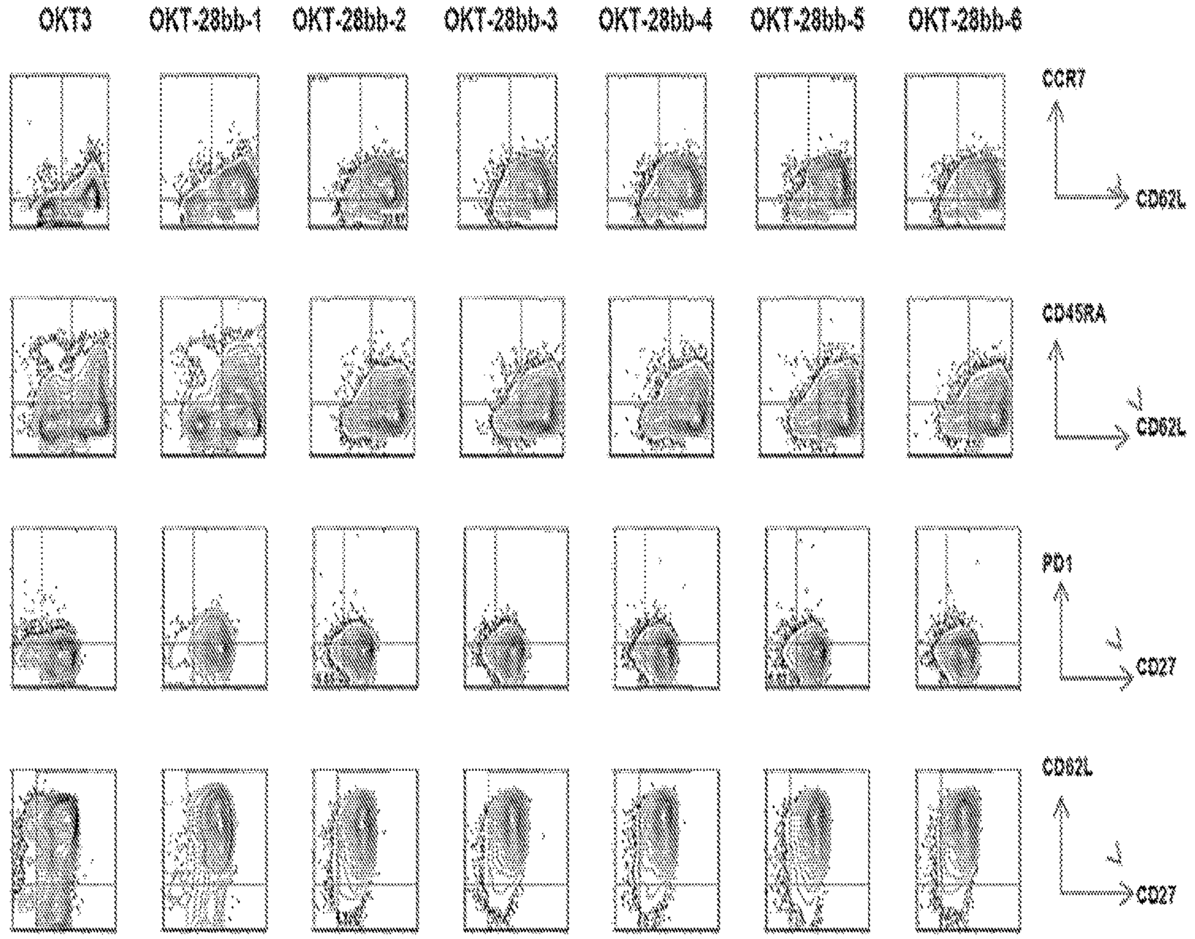
FIG. 6 is a panel of graphs showing the phenotype analysis of the expanded T cells. The phenotype of T cells expanded for 10 days by OKT-28BB or combined with other RNA electroporated T cells were compared with the phenotype of T cells expanded by OKT3 (OKT3) stimulation.

Further optimization of expanded T cells through co-electroporation with RNAs encoding costimulatory molecules, switch receptors and cytokines. To test if adding additional molecules by RNA electroporation could further enhance T cells obtained through expansion of RNA electroporated PBMCs, OKT-28BB RNA was mixed with RNAs encoding costimulatory molecules, switch receptors or cytokines in different combinations, as listed in FIG. 10. Phenotype and functionality of T cells obtained from RNA electroporated PBMCs were compared with T cells obtained from OKT3 antibody stimulated PBMCs. Phenotypic analysis is shown in FIG. 6. The T cells obtained from OKT-28BB RNA electroporation (OKT-28bb-1) displayed a central memory T cell phenotype as compared with T cells obtained from OKT3 antibody stimulation. Approximately 54.54% of the T cells obtained from OKT-28BB RNA electroporation versus about 25.08% of the T cells T cells obtained from OKT3 antibody stimulation were CCR7/CD62L double positive cells.

Moreover, electroporation of other RNAs, RNA encoding programmed cell death 1 (PD1), CD83, CD86, 4-1BBL, PD1-CD28 or IL-21, with OKT-28BB RNA increased T cell expansion. In OKT-28bb-2 and OKT-28bb-6, T cell expansion was further increased from about 64.85% (OKT-28bb-5) to about 69.21% (OKT-28bb-3). PD1 was significantly upregulated in T cells obtained from PBMCs electroporated with OKT-28BB RNA alone, whereas, about 32.37% of PD1/CD27 double positive cells were detected in T cells obtained from OKT-28BB RNA electroporated PBMCs, versus 6.24% PD1/CD27 double positive cells detected in T cells obtained from OKT3 antibody stimulated PBMCs. Co-electroporation of other RNAs during the T cell expansion step also decreased PD1 expression in some of the expanded T cell populations, OKT-28bb-6 (9.30%) and OKT-28bb-2 (14.08%).

Figure 7:
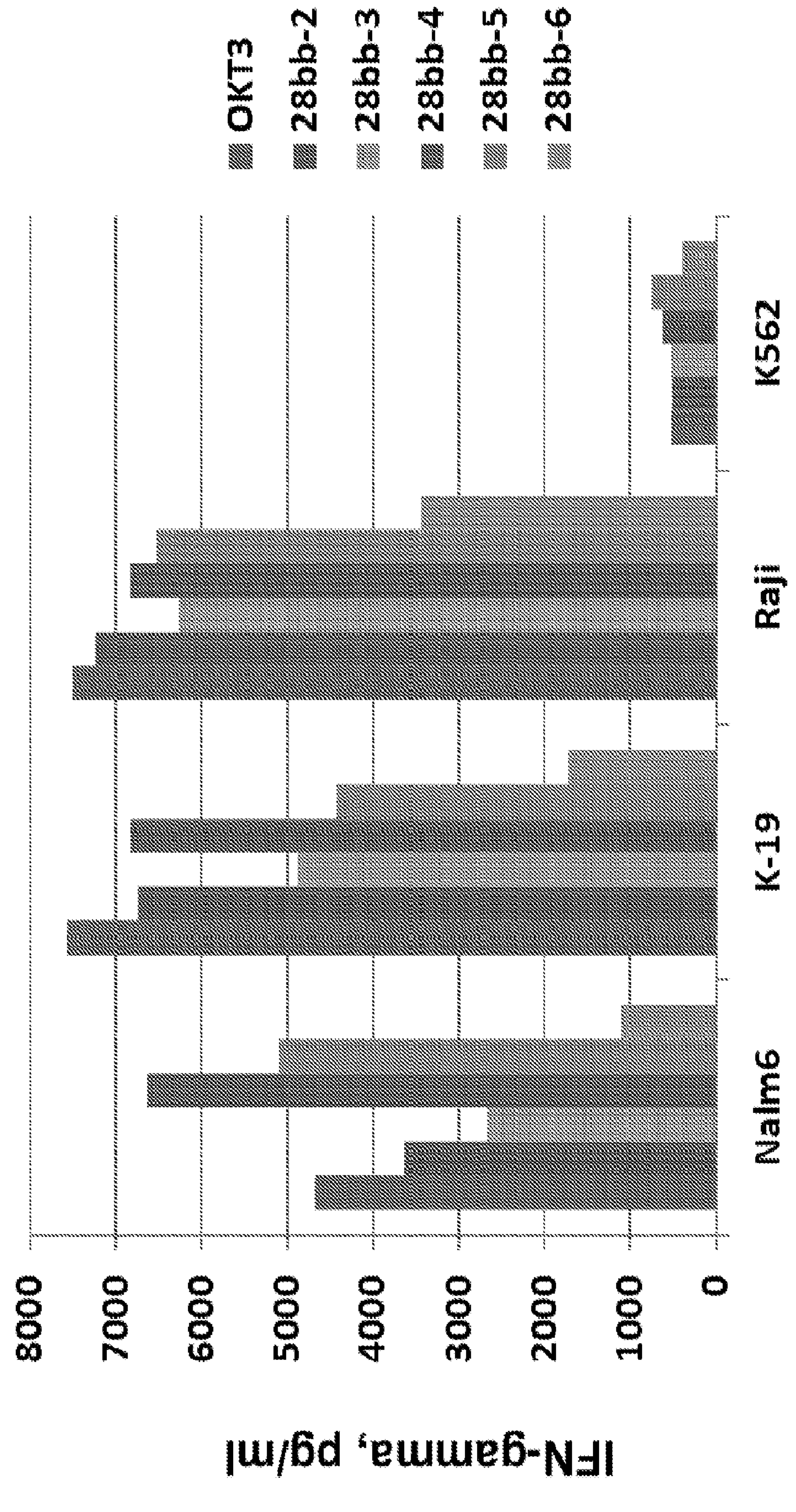
FIG. 7 is a bar graph showing levels of interferon-gamma (IFN-γ) production of T cells expanded by co-electroporation of OKT-28BB with RNA encoding other molecules and electroporated with CD19 CAR RNA, stimulated with CD19 positive cell lines for 18 hr. The levels of IFN-γ were measured by ELISA.
Figure 8:
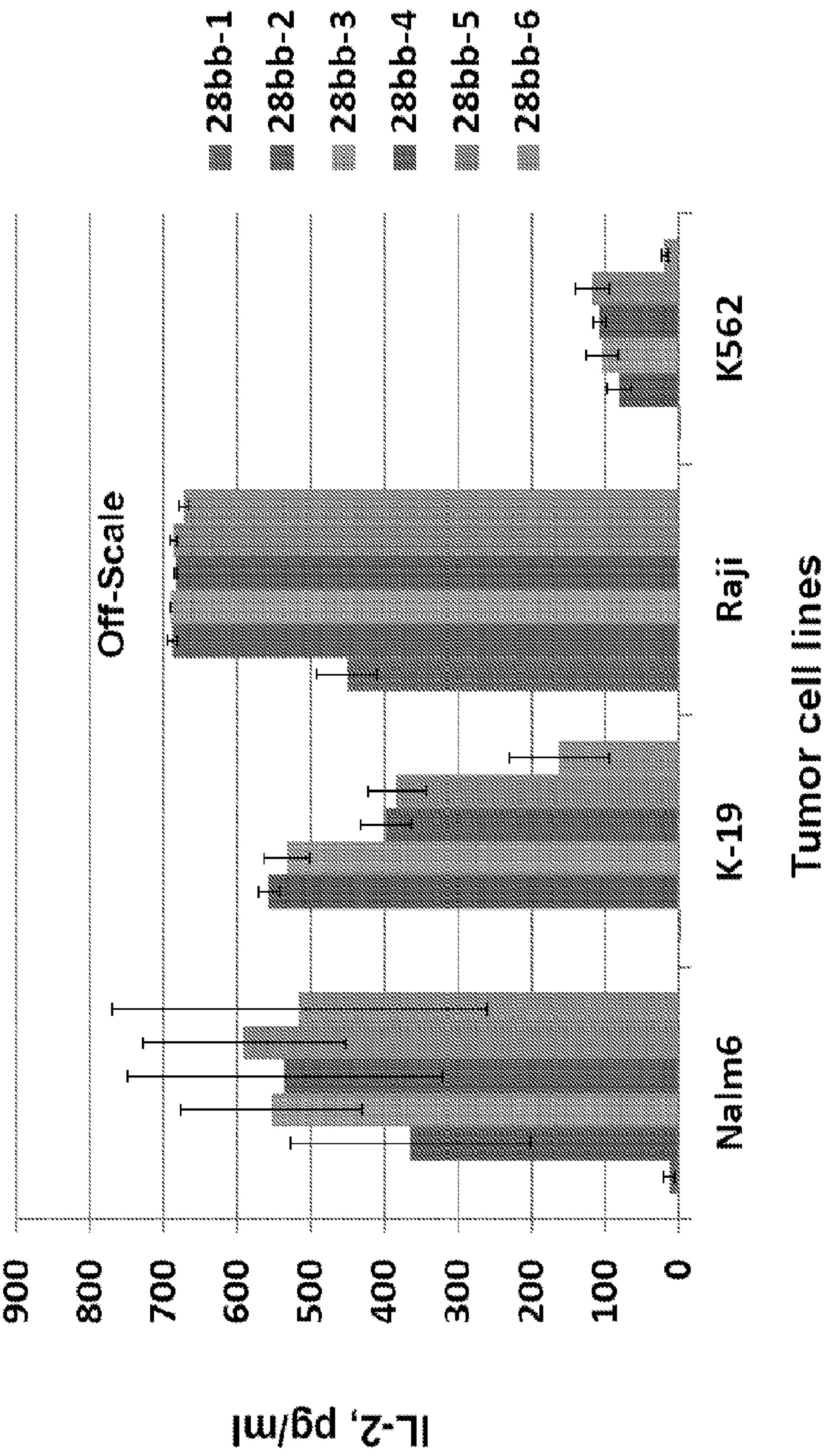
FIG. 8 is a bar graph showing levels of IL-2 production of T cells expanded by co-electroporation of OKT-28BB with RNA encoding other molecules (listed in FIG. 10) and electroporated with CD19 CAR RNA, stimulated with CD19 positive cell lines for 18 hr. The levels of IL-2 were measured by ELISA.

Cytokine production, interferon-gamma (FIG. 7) and IL-2 (FIG. 8), was assessed in the expanded T cells that were electroporated with CD19 CAR RNA (CD19 CAR T cells) and incubated with different tumor cell lines expressing CD19. Co-electroporation with other RNAs resulted in variable levels of secreted TFN-gamma from CD19 CAR RNA T cells after incubation with the different CD19 tumor cell lines. Higher levels of IL-2 were secreted by the CD19 CAR RNA T cells obtained from PBMCs electroporated with OKT-28BB RNA than CD19 CAR RNA T cells obtained from OKT3 antibody stimulated PBMCs.

Figure 9:
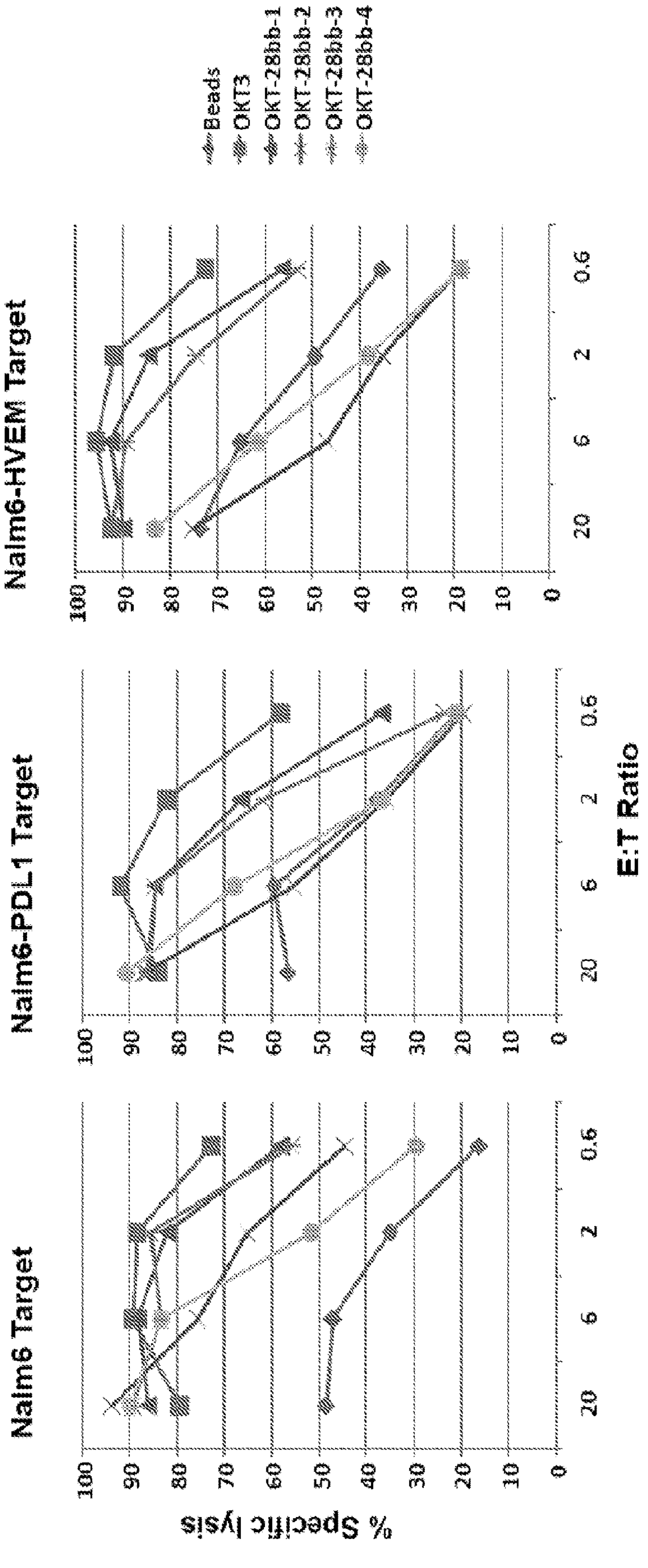
FIG. 9 is a panel of graphs illustrating T cell lytic activity tested by a cytotoxic T lymphocyte (CTL) assay for T cells expanded by co-electroporation of OKT-28BB with RNA encoding other molecules, and electroporated with CD19 CAR RNA, stimulated with CD19 positive tumor, Nalm6; Nalm6 expressed with PDL1; or Nalm6 with HVEM.

Lytic ability of the CD19 CAR RNA T cells was also determined. CD19 CAR RNA T cells were incubated with CD19 positive cell lines, Nalm6 and Nalm6 transduced with PLL1 or HVEM. Lytic activity was reduced in some CD19 CAR RNA T cells, specifically OKT-288bb-2 and OKT-28bb-4 (FIG. 9). In contrast, lytic activity in CD19 CAR RNA electroporated OKT-28bb-1 and OKT-28bb-3 T cells was as good as CD19 CAR RNA T cells obtained from OKT3 antibody stimulation of PBMCs. While CD19 CAR RNA T cells expanded by OKT-28BB RNA electroporation generated more central memory T cells, they were capable of killing the tumor cells as efficiently as OKT3 antibody stimulated T cells, which were primarily effector memory cells (FIG. 10).

Figure 11:
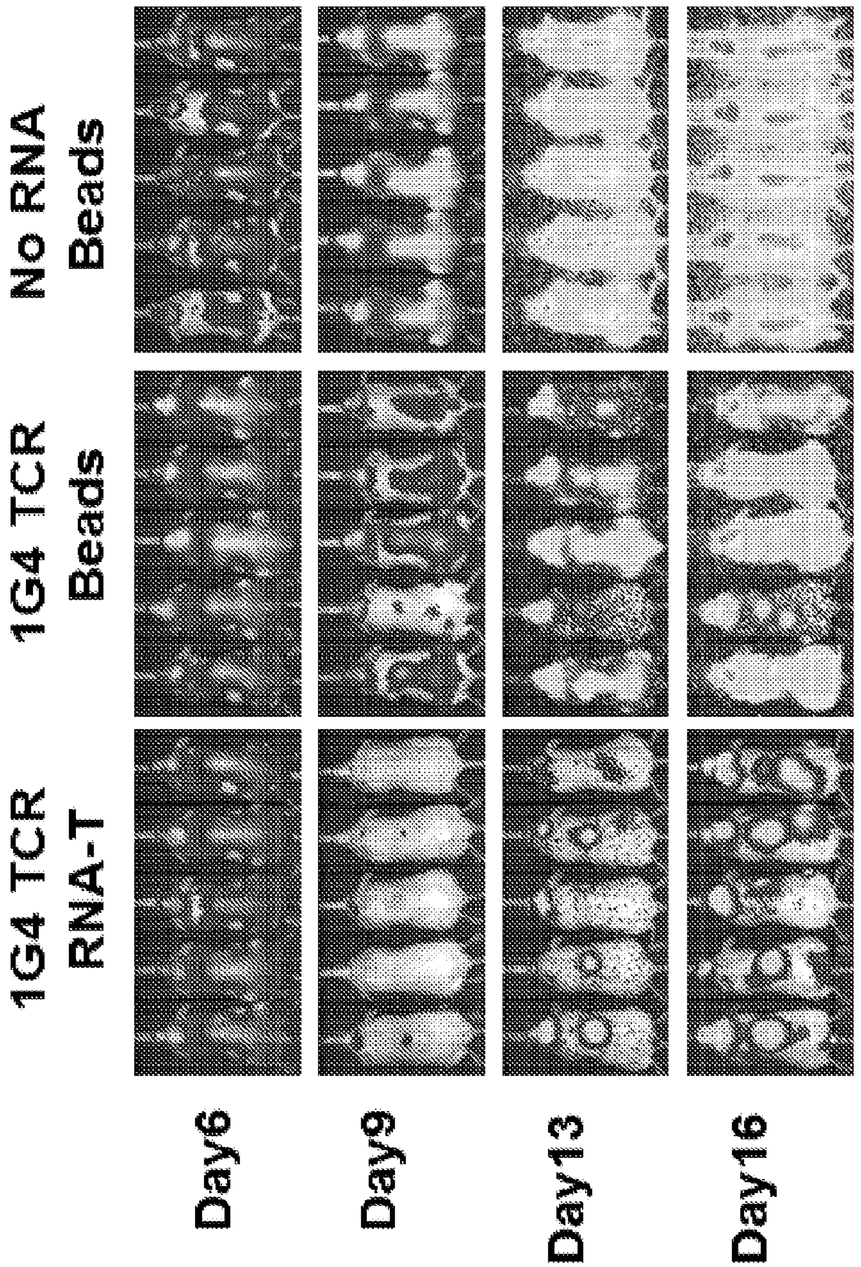
FIG. 11 is a panel of images showing NSG mice injected with 1E6 Nalm6-ESO-CBG intravenously at day 0. At day 7, $1\times10^6$ NY-ESO-T TCR (1G4 TCR) RNA electroporated OKT3-28BB RNA T cells (RNA-T) or CD3/CD28 beads T cells (Beads) were injected intravenously. Tumor burden was monitored by bioluminescence imaging. Results showed better tumor control of RNA-T cells transferred with TCR than Beads stimulated T cells.

As proof of concept, NSG mice were injected with 1E6 Nalm6-ESO-CBG (intravenously) at day 0. At day 7, $1\times10^6$ NY-ESO-T TCR (1G4 TCR) RNA electroporated OKT3-28BB RNA T cells (RNA-T) or CD3/CD28 beads T cells (Beads) were injected (intravenously). Tumor burden was monitored by bioluminescence imaging. FIG. 11 shows that better tumor control was observed in RNA-T cells transferred with TCR than Beads stimulated T cells.

Figure 12:
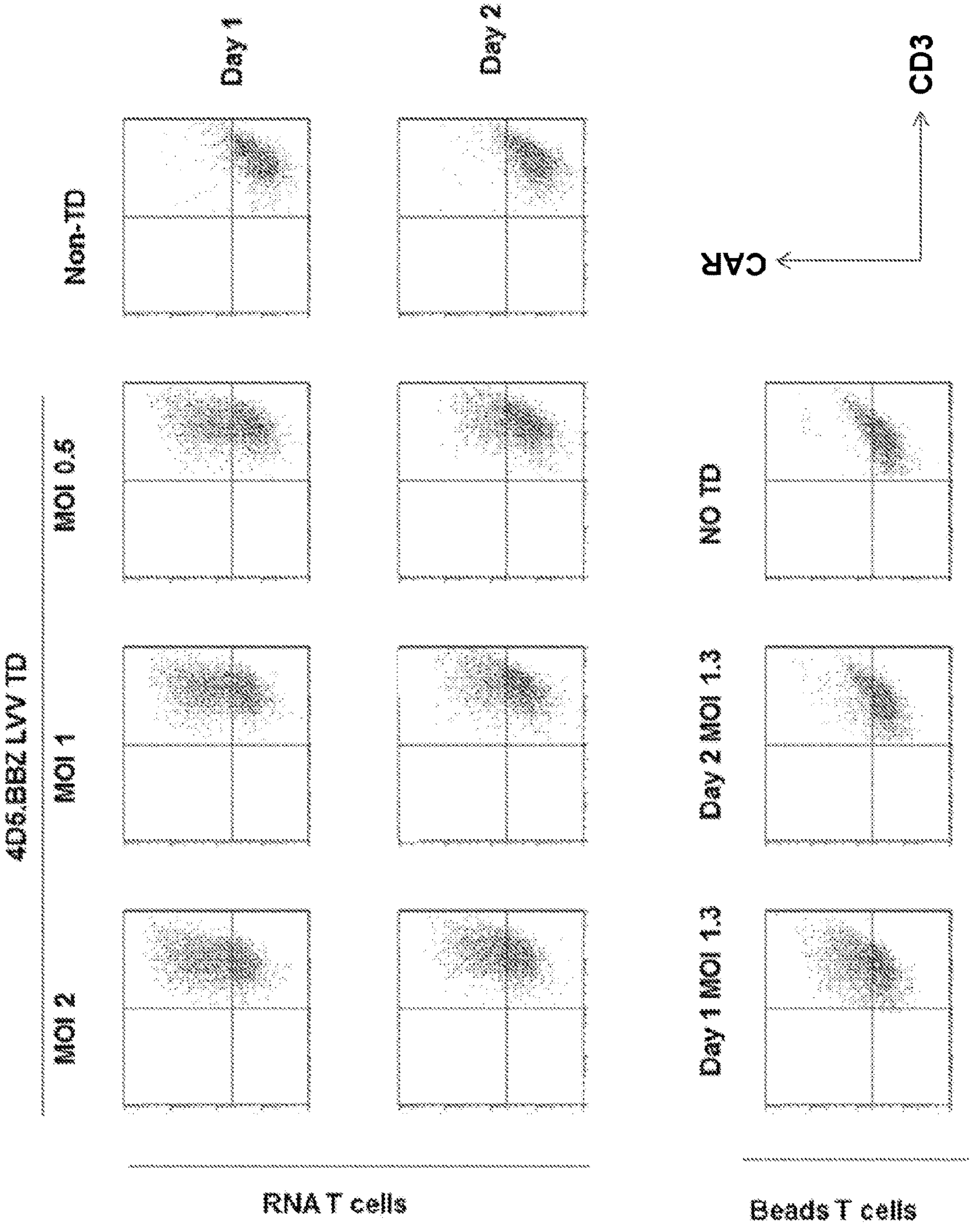
FIG. 12 is panel of graphs showing efficient lentiviral transduction of RNA-T cells. Day 1 or day 2 RNA T cells were harvested and aliquoted into a 24 well plate with 0.5 ml, 1 ml or 2 ml/well at cell concentrations of $1.5\times10^6$/ml. 0.1 ml of concentrated 4D5. BBZ lentiviral vector (at titer of $5\times10^6$/ml) was added to each well. As controls, 4D5. BBZ lentiviral vector was added to day 1 or day 2 to CD3/CD28 bead stimulated T cells at multiple of infection (MOI) as indicated. Day 9 post stimulation, the expanded T cells were subjected to flow cytometry staining for the detection of transduced CAR expression.

To test efficiency of lentiviral transduction into RNA-T cells, day 1 or day 2 RNA T cells were harvested and aliquoted into a 24 well plate with 0.5 ml, 1 ml or 2 ml/well at cell concentrations of $1.5\times10^6$/ml. 0.1 ml of concentrated 4D5. BBZ lentiviral vector (at titer of $5\times10^6$/ml) was added to each well. As controls, 4D5. BBZ lentiviral vector was added to day 1 or day 2 to CD3/CD28 bead stimulated T cells at multiple of infection (MOT) as indicated. Day 9 post stimulation, the expanded T cells were subjected to flow cytometry staining (FIG. 12) for the detection of transduced CAR expression.

Figure 13:
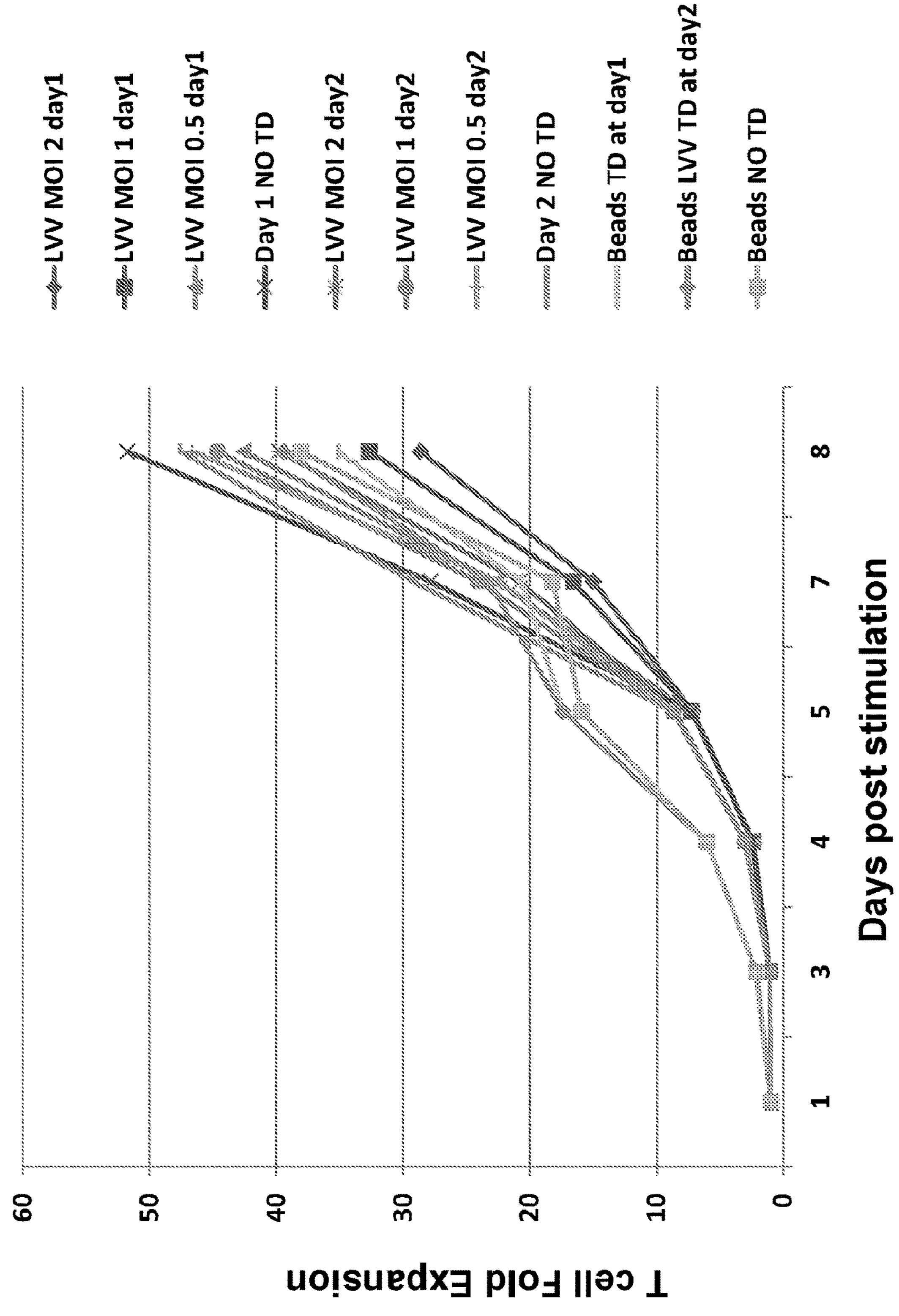
FIG. 13 is a graph showing T cell expansion of lentivirally transduced RNA T cells. The results indicated that both lentivirally transduced or non-transduced RNA T cells were expanded as efficiently as those of CD3/CD28 beads stimulated T cells.

The results shown in FIG. 13 indicate that both lcntivirally transduced or non-transduced RNA T cells were expanded as efficiently as those of CD3/CD28 beads stimulated T cells.

Figure 14:
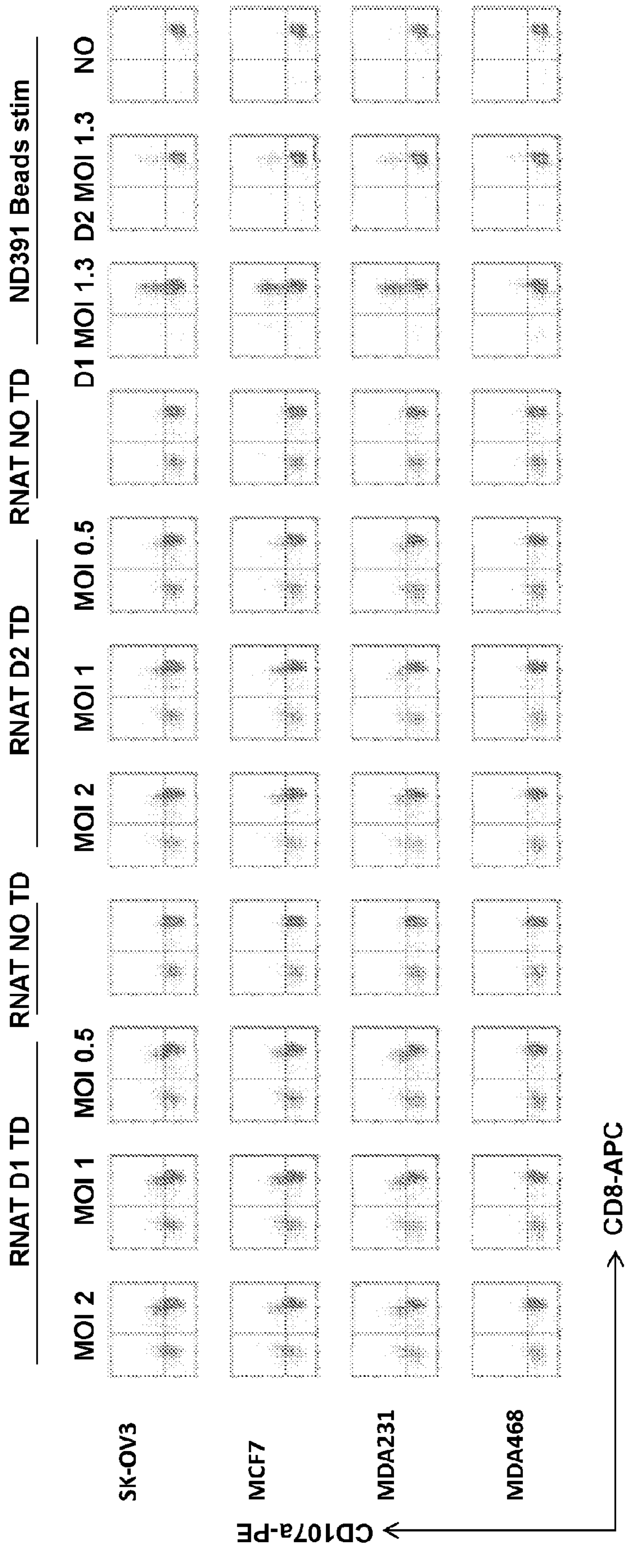
FIG. 14 is a panel of graphs showing CD107a upregulation in lentiviral transduced RNA-T cells. Lentivirally transduced RNA T cells, or Beads stimulated T cells were stimulated with Her2 positive cell lines, SK-OV3, MCF7 and MDA231, or a Her2 negative tumor line, MDA468, for 4 h, CD107a expression was detected with flow cytometry.

Lentivirally transduced RNA T cells, or Beads stimulated T cells were then stimulated with Her2 positive cell lines, SK-OV3, MCF7 and MDA231, or a Her2 negative tumor line, MDA468, for 4 h, CD107a expression was detected with flow cytometry, see FIG. 14.

Figure 15:
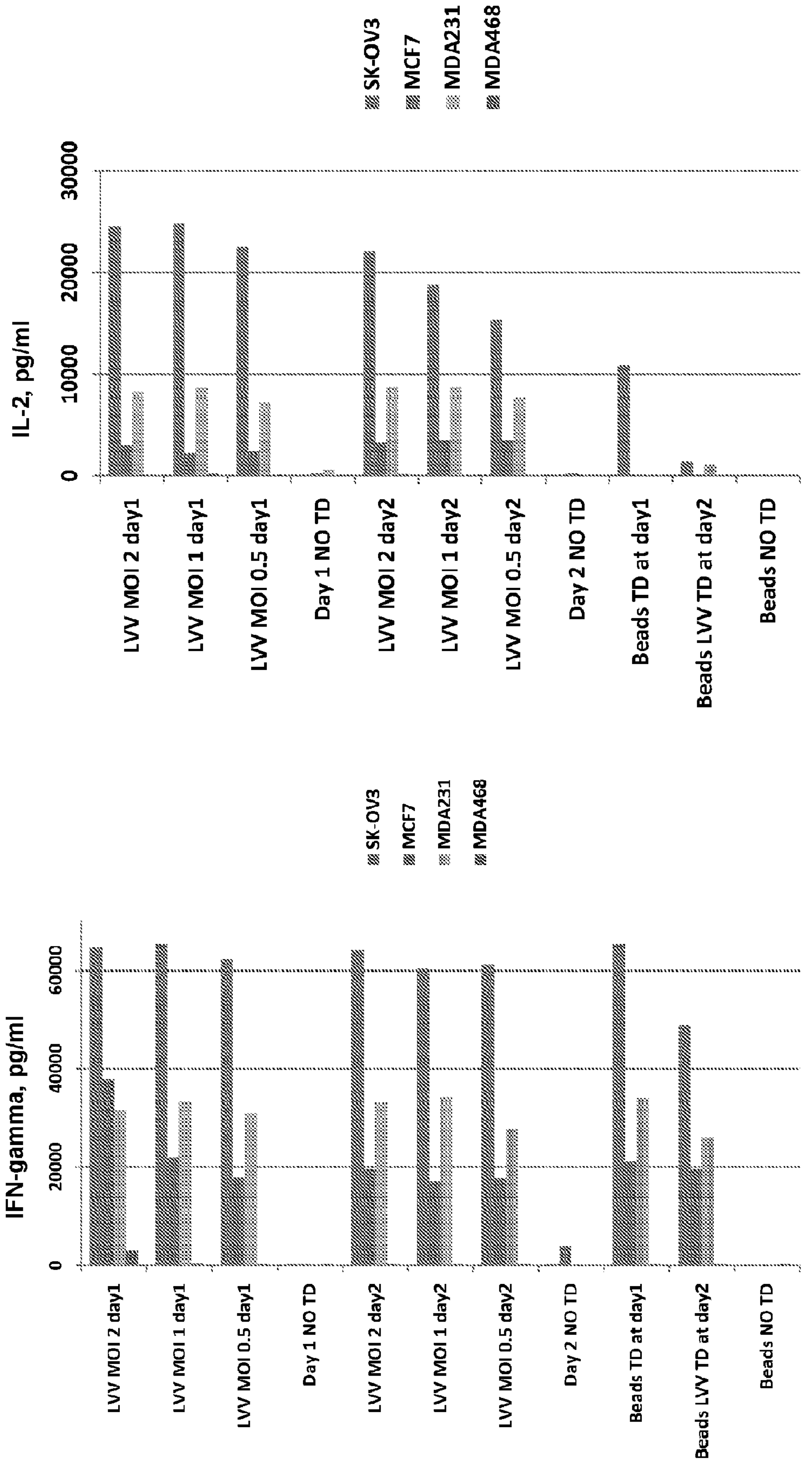
FIG. 15 is a panel of graphs showing cytokine production of lentiviral transduced RNA-T cells. Lentivirally transduced RNA T cells, or Beads stimulated T cells were stimulated with Her2 positive cell lines, SK-OV3, MCF7 and MDA231, or a Her2 negative tumor line, MDA468, and cytokine production was detected by ELISA after overnight incubation.

Cytokine production in lentiviral transduced RNA-T cells was compared to Beads stimulated T cells. Lentivirally transduced RNA T cells, or Beads stimulated T cells were stimulated with Her2 positive cell lines, SK-OV3, MCF7 and MDA231, or a Her2 negative tumor line, MDA468, for 4 h. Lentivirally transduced RNA T cells produced more IL-2 and IFN-γ than Beads stimulated T cells when cytokine levels were analyzed by ELISA (FIG. 15) after overnight incubation.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A T cell comprising a nucleic acid encoding a chimeric membrane protein comprising:
   - an extracellular domain comprising an antigen binding domain comprising an anti-CD3 antibody or fragment thereof;
   - a transmembrane domain; and
   - an intracellular domain comprising a fragment of an intracellular domain of CD28 and a fragment of an intracellular domain of 4-1BB;
   - wherein the intracellular domain does not comprise a CD3-zeta domain;
   - wherein the chimeric membrane protein is expressed on the surface of the T cell; and
   - wherein the T cell is capable of expansion to generate a population of expanded T cells upon an interaction between the anti-CD3 antibody or fragment thereof and CD3.

2. The T cell of claim 1, wherein the anti-CD3 antibody or fragment thereof is a synthetic antibody, human antibody, humanized antibody, single domain antibody, single chain variable fragment, or antigen-binding fragments thereof.

3. The T cell of claim 1, wherein the chimeric membrane protein further comprises a hinge domain.

4. The T cell of claim 1, wherein the interaction expands the T cell by at least 10-fold within 7 to 10 days of the interaction.

5. The T cell of claim 1, wherein the interaction expands the T cell by about 20 fold to about 50 fold.

6. The T cell of claim 1, wherein the anti-CD3 antibody or fragment thereof is an anti-CD3 single chain variable fragment (scFv), the transmembrane domain is a CD28 transmembrane domain, and the chimeric membrane protein further comprises a CD8 hinge.

7. The T cell of claim 1, wherein the anti-CD3 antibody or the fragment thereof is OKT3, H5L1, or a fragment thereof.

8. The T cell of claim 1, wherein the anti-CD3 antibody or the fragment thereof is a scFv of OKT3 or H5L1.

9. The T cell of claim 1 further comprising a chimeric antigen receptor (CAR).

10. A population of T cells comprising the T cell of claim 1.

11. The population of T cells of claim 10, wherein from 54.54% to 69.21% of the T cells express CCR7 protein, CD62L protein, and CD45RO protein.

* * * * *

SEQUENCE LISTING

```
Sequence total quantity: 7
SEQ ID NO: 1           moltype = DNA  length = 1263
FEATURE                Location/Qualifiers
source                 1..1263
                       mol_type = other DNA
                       organism = Homo sapiens
SEQUENCE: 1
atggcactgc ccgtgaccgc cctcctcctg cccctcgcgc tactcctgca cgccgccaga  60
ccccaggtgc agctgcagca gagtggcgct gagctggccc gccccggcgc ctccgtgaag  120
atgtcctgca aggctagtgg gtataccttc accaggtata ctatgcactg ggtgaagcag  180
cgtccggggc aggggctcga gtggatcggc tacatcaatc cctcccgcgg ctacaccaat  240
tacaaccaga agttcaagga taaggccacg ctgaccacag acaagagtag ctccacggcc  300
tacatgcagt tatcaagtct gacctctgag gactccgctg tgtactattg tgcgaggtac  360
tacgacgacc actactgtct ggactactgg ggccaaggca caaccctgac tgtaagttcc  420
tccggcggcg gggggtccgg cggcggcggc tccggcgggg ggggtagtat cgtgctgaca  480
cagagtcccg caatcatgtc cgcaagcccc ggagagaagg tgaccatgac gtgtagtgct  540
tccagctccg tgtcctatat gaactggtac cagcagaaat ccgggacttc ccccaagaga  600
tggatctacg acaccagtaa gctggccagt ggcgtgcctg cacacttccg cggcagtggc  660
tccggcacta gttacagtct caccatctcc gggatggaag ctgaggacgc cgctacctac  720
tactgccagc agtggagctc gaacccattc accttcggtt cggggaccaa gctcgagatc  780
aacagggcgg ccgccaccac gacgccagcg ccgcgaccac caacaccggc gcccaccatc  840
gcgtcgcagc ccctgtccct gcgcccagag gcgtgccggc cagcggcggg gggcgcagtg  900
cacacgaggg ggctggactt cgcctgtgat ttttgggtgc tggtggtggt tggtggagtc  960
ctggcttgct atagcttgct agtaacagtg gcctttatta ttttctgggt gaggagtaag  1020
aggagcaggc tcctgcacag tgactacatg aacatgactc cccgccgccc cgggcccacc  1080
cgcaagcatt accagcccta tgccccacca cgcgacttcg cagcctatcg ctccaaacgg  1140
ggcagaaaga aactcctgta tatattcaaa caaccattta tgagaccagt acaaactact  1200
caagaggaag atggctgtag ctgccgattt ccagaagaag aagaaggagg atgtgaactg  1260
taa                                                                1263

SEQ ID NO: 2           moltype = DNA  length = 1269
FEATURE                Location/Qualifiers
source                 1..1269
                       mol_type = other DNA
                       organism = Homo sapiens
SEQUENCE: 2
atggcactgc ccgtgaccgc cctcctcctg cccctcgcgc tactcctgca cgccgccaga  60
cccgacgtgc agctcgtgca gtccggggcc gaggtcaaga agccaggcgc ctccgtgaaa  120
gtgtcgtgca aggcttccgg gtacacgttc acgaggtaca cgatgcactg ggtgcggcag  180
gcccccggcc agggcctgga gtggatcggc tacatcaatc cctctcgcgg ctacacaaat  240
tacgccgact ccgtgaaagg ccggttcacc attactaccg acaagtccac cagcactgcc  300
tatatggagc tgtccagtct ccgcagcgag gatacggcca cgtactactg tgcccgatac  360
tacgacgacc actactgcct ggactactgg gggcagggaa ccaccgtgac agtgtcttcc  420
ggggaaggga ccagcactgg ctcgggcggc tccgggggtt ccgggggtgc cgacgatatc  480
cagatgaccc aaagtcccag ctcgctgagc gccagtgtcg gcgatcgcgt gaccatcacc  540
```

```
tgccgcgcgt ctcagtctgt gtcctacatg aactggtacc agcaaaagcc cggtaaggcc  600
cccaagcgct ggatctacga caccagcaaa gtcgcctcgg gcgtccccgc ccggttcagc  660
gggtccgggt ccgggacaga ttactcgctc acgatcaact cgctggaggc ggaagacgcc  720
gcaacttatt attgccagca gtggagttcc aaccctctga ccttcggggg tggcacgaag  780
gtggaaatca aggcggccgc caccacgacg ccagcgccgc gaccaccaac accggcgccc  840
accatcgcgt cgcagcccct gtccctgcgc ccagaggcgt gccggccagc ggcggggggc  900
gcagtgcaca cgagggggct ggacttcgcc tgtgattttt gggtgctggt ggtggttggt  960
ggagtcctgg cttgctatag cttgctagta acagtggcct ttattatttt ctgggtgagg  1020
agtaagagga gcaggctcct gcacagtgac tacatgaaca tgactccccg ccgccccggg  1080
cccacccgca agcattacca gccctatgcc ccaccacgcg acttcgcagc ctatcgctcc  1140
aaacggggca gaaagaaact cctgtatata ttcaaacaac catttatgag accagtacaa  1200
actactcaag aggaagatgg ctgtagctgc cgatttccag aagaagaaga aggaggatgt  1260
gaactgtaa                                                         1269

SEQ ID NO: 3           moltype = DNA  length = 624
FEATURE                Location/Qualifiers
source                 1..624
                       mol_type = other DNA
                       organism = Homo sapiens
SEQUENCE: 3
atggcgcgcg gcctccagct tctgctcctg agctgcgcct acagcctggc tcccgcgacg  60
ccggaggtga aggtggcttg ctccgaagat gtggacttgc cctgcaccgc cccctgggat  120
ccgcaggttc cctacacggt ctcctgggtc aagttattgg agggtggtga agagaggatg  180
gagacacccc aggaagacca cctcagggga cagcactatc atcagaaggg gcaaaatggt  240
tctttcgacg cccccagccg ccatgaaagg ccctattccc tgaagatccg aaacactacc  300
agctgcaact cggggacata caggtgcact ctgcaggacc cggatgggca gagaaaccta  360
agtggcaagg tgatcttgag agtgacagga tgccctgcac agcgtaaaga agagactttt  420
aagaaataca gagcggagat tgtcctgctg ctggctctgg ttatttttcta cttaacactc  480
atcattttca cttgtaagtt tgcacggcta cagagtatct tcccagattt ttctaaagct  540
ggcatggaac gagcttttct cccagttacc tccccaaata agcatttagg gctagtgact  600
cctcacaaga cagaactggt atga                                       624

SEQ ID NO: 4           moltype = DNA  length = 990
FEATURE                Location/Qualifiers
source                 1..990
                       mol_type = other DNA
                       organism = Homo sapiens
SEQUENCE: 4
atggatcccc agtgcactat gggactgagt aacattctct ttgtgatggc cttcctgctc  60
tctggtgctg ctcctctgaa gattcaagct tatttcaatg agactgcaga cctgccatgc  120
caatttgcaa actctcaaaa ccaaagcctg agtgagctag tagtattttg gcaggaccag  180
gaaaacttgg ttctgaatga ggtatactta ggcaaagaga aatttgacag tgttcattcc  240
aagtatatgg gccgcacaag ttttgattcg gacagttgga ccctgagact tcacaatctt  300
cagatcaagg acaagggctt gtatcaatgt atcatccatc acaaaaagcc cacaggaatg  360
attcgcatcc accagatgaa ttctgaactg tcagtgcttg ctaacttcag tcaacctgaa  420
atagtaccaa tttctaatat aacagaaaat gtgtacataa atttgacctg ctcatctata  480
cacggttacc cagaacctaa gaagatgagt gttttgctaa gaaccaagaa ttcaactatc  540
gagtatgatg gtgttatgca gaaatctcaa gataatgtca cagaactgta cgacgtttcc  600
atcagcttgt ctgtttcatt ccctgatgtt acgagcaata tgaccatctt ctgtattctg  660
gaaactgaca agacgcggct tttatcttca cctttctcta tagagcttga ggaccctcag  720
cctcccccag accacattcc ttggattaca gctgtacttc caacagttat tatatgtgtg  780
atggttttct gtctaattct atggaaatgg aagaagaaga agcggcctcg caactcttat  840
aaatgtggaa ccaacacaat ggagagggaa gagagtgaac agaccaagaa aagagaaaaa  900
atccatatac ctgaaagatc tgatgaagcc cagcgtgttt ttaaaagttc gaagacatct  960
tcatgcgaca aaagtgatac atgtttttaa                                  990

SEQ ID NO: 5           moltype = DNA  length = 765
FEATURE                Location/Qualifiers
source                 1..765
                       mol_type = other DNA
                       organism = Homo sapiens
SEQUENCE: 5
atggaatacg cctctgacgc ttcactggac cccgaagccc cgtggcctcc cgcgccccgc  60
gctcgcgcct gccgcgtact gccttgggcc ctggtcgcgg ggctgctgct gctgctgctg  120
ctcgctgccg cctgcgccgt cttcctcgcc tgcccctggg ccgtgtccgg ggctcgcgcc  180
tcgcccggct ccgcggccag cccgagactc cgcgagggtc ccgagctttc gcccgacgat  240
cccgccggcc tcttggacct gcggcagggc atgtttgcgc agctggtggc ccaaaatgtt  300
ctgctgatcg atgggcccct gagctggtac agtgacccag gcctggcagg cgtgtccctg  360
acggggggcc tgagctacaa agaggacacg aaggagctgg tggtggccaa ggctggagtc  420
tactatgtct tctttcaact agagctgcgg cgcgtggtgg ccggcgaggg ctcaggctcc  480
gtttcacttg cgctgcacct gcagccactg cgctctgctg ctggggccgc cgccctggct  540
ttgaccgtgg acctgccacc cgcctcctcc gaggctcgga actcggcctt cggtttccag  600
ggccgcttgc tgcacctgag tgccggccag cgcctgggcg tccatcttca cactgaggcc  660
agggcacgcc atgcctggca gcttacccag ggcgccacag tcttgggact cttccgggtg  720
acccccgaaa tcccagccgg actcccttca ccgaggtcgg aataa                765

SEQ ID NO: 6           moltype = DNA  length = 717
FEATURE                Location/Qualifiers
source                 1..717
```

-continued

```
                        mol_type = other DNA
                        organism = Homo sapiens
SEQUENCE: 6
atgcagatcc cacaggcgcc ctggccagtc gtctgggcgg tgctacaact gggctggcgg  60
ccaggatggt tcttagactc cccagacagg ccctggaacc cccccacctt ctccccagcc  120
ctgctcgtgg tgaccgaagg ggacaacgcc accttcacct gcagcttctc caacacatcg  180
gagagcttcg tgctaaactg gtaccgcatg agccccagca accagacgga caagctggcc  240
gccttccccg aggaccgcag ccagcccggc caggactgcc gcttccgtgt cacacaactg  300
cccaacgggc gtgacttcca catgagcgtg gtcagggccc ggcgcaatga cagcggcacc  360
tacctctgtg gggccatctc cctggccccc aaggcgcaga tcaaagagag cctgcgggca  420
gagctcaggg tgacagagag aagggcagaa gtgcccacag cccaccccag ccccctcaccc  480
aggccagccg gccagttcca aaccctggtg ttttgggtgc tggtggtggt tggtggagtc  540
ctggcttgct atagcttgct agtaacagtg gcctttatta ttttctgggt gaggagtaag  600
aggagcaggc tcctgcacag tgactacatg aacatgactc cccgccgccc cgggcccacc  660
cgcaagcatt accagcccta tgccccacca cgcgacttcg cagcctatcg ctcctaa     717

SEQ ID NO: 7            moltype = DNA  length = 1461
FEATURE                 Location/Qualifiers
source                  1..1461
                        mol_type = other DNA
                        organism = Homo sapiens
SEQUENCE: 7
atggccttac cagtgaccgc cttgctcctg ccgctggcct tgctgctcca cgccgccagg  60
ccggacatcc agatgacaca gactacatcc tccctgtctg cctctctggg agacagagtc  120
accatcagtt gcagggcaag tcaggacatt agtaaatatt taaattggta tcagcagaaa  180
ccagatggaa ctgttaaact cctgatctac catacatcaa gattacactc aggagtccca  240
tcaaggttca gtggcagtgg gtctggaaca gattattctc tcaccattag caacctggag  300
caagaagata ttgccactta cttttgccaa cagggtaata cgcttccgta cacgttcgga  360
ggggggacta agttggaaat aacaggtggc ggtggctcgg gcggtggtgg gtcgggtggc  420
ggcggatctg aggtgaaact gcaggagtca ggacctggcc tggtggcgcc ctcacagagc  480
ctgtccgtca catgcactgt ctcaggggtc tcattacccg actatggtgt aagctggatt  540
cgccagcctc cacgaaaggg tctggagtgg ctgggagtaa tatggggtag tgaaaccaca  600
tactataatt cagctctcaa atccagactg accatcatca aggacaactc caagagccaa  660
gttttcttaa aaatgaacag tctgcaaact gatgacacag ccatttacta ctgtgccaaa  720
cattattact acggtggtag ctatgctatg gactactggg gtcaaggaac ctcagtcacc  780
gtctcctcaa ccacgacgcc agcgccgcga ccaccaacac cggcgcccac catcgcgtcg  840
cagcccctgt ccctgcgccc agaggcgtgc cggccagcgg cggggggcgc agtgcacacg  900
agggggctgg acttcgcctg tgatatctac atctgggcgc ccttggccgg gacttgtggg  960
gtccttctcc tgtcactggt tatcaccctt tactgcaaac ggggcagaaa gaaactcctg  1020
tatatattca aacaaccatt tatgagacca gtacaaacta ctcaagagga agatggctgt  1080
agctgccgat ttccagaaga agaagaagga ggatgtgaac tgagagtgaa gttcagcagg  1140
agcgcagacg cccccgcgta ccagcagggc cagaaccagc tctataacga gctcaatcta  1200
ggacgaagag aggagtacga tgttttggac aagagacgtg gccgggaccc tgagatgggg  1260
ggaaagccga gaaggaagaa ccctcaggaa ggcctgtaca atgaactgca gaaagataag  1320
atggcggagg cctacagtga gattgggatg aaaggcgagc gccggagggg caaggggcac  1380
gatggccttt accagggtct cagtacagcc accaaggaca cctacgacgc ccttcacatg  1440
caggccctgc cccctcgcta a                                           1461
```